United States Patent [19]

Billhardt-Troughton et al.

[11] Patent Number: 5,602,146

[45] Date of Patent: Feb. 11, 1997

[54] 4-IMINOQUINOLINES, PROCESSES FOR THEIR PREPARATION, AND THEIR USE

[75] Inventors: Uta-Maria Billhardt-Troughton, Raleigh, N.C.; Manfred Rösner, Eppstein/Taunus; Rudolph Bender, Bad Soden am Taunus; Christoph Meichsner, Liederbach, all of Germany

[73] Assignee: Hoechst Aktiengesellschaft, Frankfurt am Main, Germany

[21] Appl. No.: 372,828

[22] Filed: Jan. 13, 1995

Related U.S. Application Data

[63] Continuation of Ser. No. 80,845, Jun. 24, 1993, abandoned.

[30] Foreign Application Priority Data

Jun. 27, 1992 [DE] Germany ............ 42 21 210.3

[51] Int. Cl.[6] ............ A61K 31/47; C07D 215/04; C07D 215/12; C07D 215/16
[52] U.S. Cl. ............ 514/312; 514/278; 546/15; 546/158
[58] Field of Search ............ 546/15, 158; 514/312, 514/278

[56] References Cited

FOREIGN PATENT DOCUMENTS

| | | |
|---|---|---|
| 14853/92 | 10/1992 | Australia . |
| 0100200 | 2/1984 | European Pat. Off. . |
| 0476544A1 | 3/1992 | European Pat. Off. . |
| 0509398 | 10/1992 | European Pat. Off. . |
| WOA8703200 | 6/1987 | WIPO . |

OTHER PUBLICATIONS

A. Desvignes et al., Recherche sur les Aminoquinoleines. XVIII. Activite antibacterienne et antifongique in vitro d'alkylamino–4 quinoleines a longues chaines (5[e] memoire), Annales Pharmaceutiques Francaises, 35(7–8):239–247 (1977).

P. Rajamanickam et al., A New Synthesis of Dictamnine, Evolitrine & 6–Methyldictamnine, Indian Journal of Chemistry, vol. 26B:910–913 (Oct. 1987).

R. Hull et al., Reactions of Heterocycles with Thiophosgene. Part V. 7–Chloro–1,2–1,2–dihydro–4–methoxy–2–thioxoquinoline–3–carbaldehyde, a Prodct from 7–Chloro–4–methoxyquinoline, J. Chemical Society Trans 1, 22:2271–2280 (1975).

S. Renault et al., Recherche sur les Aminoquinoleines, XVI: alkylamino–4 quinoleines et quinaldines a longues chaines a activite amoebicide potentielle (4[e] memoire): influence de substituants nucleaires electrodonneurs, Eur. J. Med. Chem., 11(6):561–565 (1976).

Abstract of Study of Aminquinolines, XVI: Long–Chain 4–alkylaminoquinolines and Quinaldines with Potential Amebicide Activity. Part 4: Effect of Nuclear Electron Donor Substituents, CA87(3):22980t, 1976.

Abstract of Aminoquinolines. XVIII. In Vitro Antibacterial and Antifungal Activity of Long Chain 4–alkyaminoquinolines, CA88(13):83971h, 1977.

Abstract of NZ 220168, Mochida et al., "1–Acyl–2–3–Dihydro–4(1H)–Quinolinone–4–Oxime Derivatives", New Zealand Patent Office Journal, No. 1329, vol. 79, Issue No. 1, published Feb. 26, 1990.

"Formation of Homopiperazine Rings by the Lithium Aluminum Hydride Catalyzed Rearrangement of Some Piperidone Oximes in the Phenothiazine Series", Harfenist et al., J. Amer. Chem. Soc., 80:6080–6083(1958).

"Synthetic Studies on Pyrroloquinolines, Part IV. Preparation of Hydrogenated 3a–Methylpyrrolo[3,2–c]quinolines", Tanaka et al., J. C. S. Perkin I, 2110–2113(1974).

(List continued on next page.)

*Primary Examiner*—Warren C. Ivy
*Assistant Examiner*—D. Margaret M. Mach
*Attorney, Agent, or Firm*—Finnegan, Henderson, Farabow, Garrett & Dunner, L.L.P.

[57] ABSTRACT

Compounds of the formula I

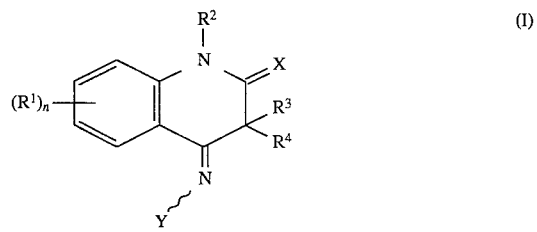

and tautomeric forms thereof, of the formula Ia,

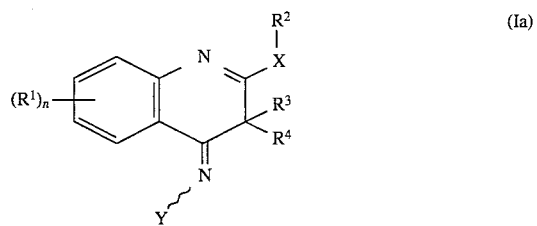

Ib and Ic

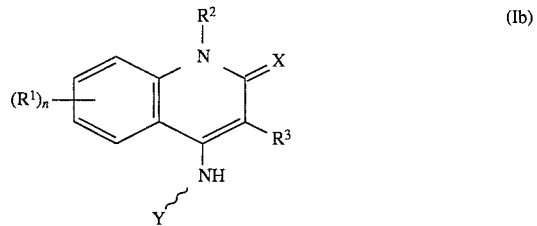

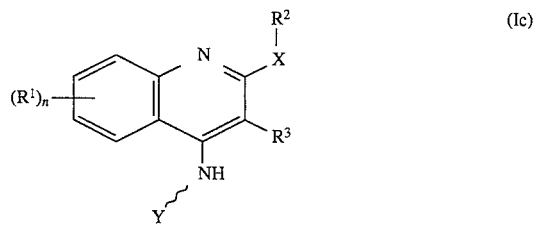

in which the substituents R1–R4 and X and Y have the meanings given; have an antiviral activity.

1 Claim, No Drawings

OTHER PUBLICATIONS

"Ring Closure of 3-Acetyl-4-azido-2-quinolones to Isoxazolor[4,3-c]quinolones", Roschger et al., Liebigs Ann. Chem., 821–823(1990).

"Thermal Cyclization of 4-Azido-3-formyl-2-quinolones to Isoxazolo[4,3-c]quinolones", Roschger et al., Liebigs Ann. Chem., 401–403(1991).

"β-Amino Ketones. Synthesis and Some Biological Activities in Mice of 3,3-Dialkyl-1,2,3,4-tetrahydro-4-quinolinones and Related Mannich Bases", Daruwala et al., *Journal of Medicinal Chemistry*, 17(8):819–824(1974).

"The Chemistry of Isatoic Anhydride", Coppola, G. M., Synthesis, 505–536 (1980).

C. Podesva et al, "Synthesis and Chemistry . . . ", Canadian J. of Chem, 46, 435–439, 1968.

4-IMINOQUINOLINES, PROCESSES FOR THEIR PREPARATION, AND THEIR USE

This application is a continuation of application Ser. No. 08/080,845 filed Jun. 24, 19993, now abandoned.

The present invention relates to 4-iminoquinolines, processes for their preparation, and their use.

Compounds related to iminoquinolines but having other fused-on rings were mentioned in a publication from the year 1958 (M. Harfenist and E. Magnien, J. Amer. Chem. Soc. 1958, 80, 6080) as intermediate compounds in a synthesis. Further works describe the preparation of pyrrolo [3,2-c]quinolinones (T. Tanaka, N. Taga, M. Miyazaki and I. Iijima, J. C. S. Perkin Trans. I 1974, 2110) and isoxazolo [4,3-c]quinolinones (P. Roschger and W. Stadlbauer, Liebigs Ann. Chem. 1990, 821; ibid 1991, 401). However, no pharmacologically interesting activity has yet been detected for these compounds. Pyrazolo[4,3c]quinolinones (EP 0476544 A1) having an antiinflammatory action have recently been described.

It has now been found, surprisingly, that certain 4-iminoquinolines have a high anti-viral activity.

The invention accordingly relates to compounds of the Formula I

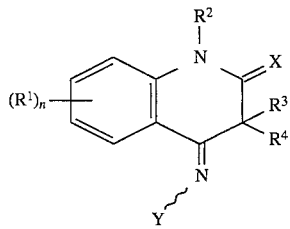

and tautomeric forms thereof, of the formula Ia

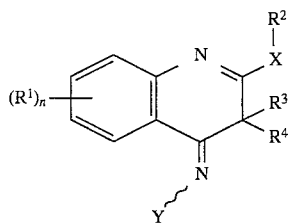

Ib and Ic

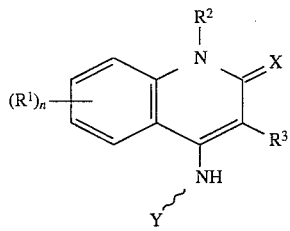

in which:
1) n is
   zero,
   one,
   two,
   three
   or four, the individual substituents R1 independently of one another are fluorine, chlorine, bromine, iodine, trifluoromethyl, trifluoromethoxy, hydroxyl, alkyl, cycloalkyl, alkoxy, alkoxy(alkoxy), alkylthio, alkylsulfinyl, alkylsulfonyl, nitro, amino, azido, alkylamino, dialkylamino, piperidino, morpholino, 1-pyrrolidinyl, acyl, acyloxy, acylamino, cyano, carbamoyl, carboxyl, alkyloxycarbonyl, hydroxysulfonyl or sulfamoyl or a phenyl, phenoxy, phenoxycarbonyl, phenylthio, phenylsulfinyl, phenylsulfonyl, phenoxysulfonyl, phenylbenzoyl, heteroaroyl, heteroaryl or heteroarylmethyl radical which is optionally substituted by up to five radicals R5 which are independent of one another, in which R5 can be fluorine, chlorine, bromine, iodine, cyano, trifluoromethyl, trifluoromethoxy, nitro, amino, azido, alkyl, cycloalkyl, alkoxy, alkylthio, alkylsulfinyl, alkylsulfonyl, alkylamino, dialkylamino, alkyloxycarbonyl, phenyl, phenoxy or heteroaryl, X is oxygen, sulfur, selenium or substituted nitrogen N—R2 or N—O R2, in which R2 can have the meanings given below, Y is R6, O—R6, S—R6, N—R6R7, N=C—R6R7 or C—R6R7R8, in which R6, R7 and R8 can have the meanings given below, R2, R6, R7 and R8 can be identical or different and can be, independently of one another, hydrogen, alkyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkenyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkynyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkenyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkyl)-(alkyl), which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkyl thio, alkylsulfonyl, phenylsulfonyl, oxo, thioxo, carboxyl or carbamoyl;

(cycloalkenyl)-(alkyl), which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkylcarbonyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkenylcarbonyl, which is optionally substituted by fluorine, chlorine or hydroxyl, alkoxy, oxo or phenyl;

(cycloalkyl)carbonyl, which is optionally substituted by fluorine, chlorine or hydroxyl, alkoxy, oxo or phenyl;

(cycloalkenyl)carbonyl, which is optionally substituted by fluorine, chlorine or hydroxyl, alkoxy, oxo or phenyl;

(cycloalkyl)-(alkyl)carbonyl, which is optionally substituted by fluorine, chlorine or hydroxyl, alkoxy, oxo or phenyl;

(cycloalkenyl)-(alkyl)carbonyl, which is optionally substituted by fluorine, chlorine or hydroxyl, alkoxy, oxo or phenyl;

alkyloxycarbonyl, which is optionally substituted by fluorine, chlorine, bromine, hydroxyl, alkoxy, alkylamino, dialkylamino or alkylthio;

alkenyloxycarbonyl, which is optionally substituted by fluorine, chlorine, hydroxyl, alkoxy, oxo or phenyl;

alkynyloxycarbonyl, which is optionally substituted by fluorine, chlorine, hydroxyl, alkoxy, oxo or phenyl;

alkylthiocarbonyl, which is optionally substituted by fluorine, chlorine, hydroxyl, alkoxy, oxo or phenyl;

alkenylthiocarbonyl, which is optionally substituted by fluorine, chlorine, hydroxyl, alkoxy, oxo or phenyl;

alkylamino- or dialkylaminocarbonyl, which is optionally substituted by fluorine, chlorine, hydroxyl, alkoxy, oxo or phenyl;

alkenylamino- or dialkenylaminocarbonyl, which is optionally substituted by fluorine, chlorine, hydroxyl, alkoxy, oxo or phenyl;

alkylsulfonyl, which is optionally substituted by fluorine, chlorine, hydroxyl, alkoxy, alkylthio, oxo or phenyl;

alkenylsulfonyl, which is optionally substituted by fluorine, chlorine, hydroxyl, alkoxy, oxo or phenyl;

or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, aryl-alkenyl, arylalkynyl, arylalkylcarbonyl, arylalkenylcarbonyl or arylalkoxycarbonyl, which are substituted by up to five radicals R5 which are independent of one another, in which R5 is as defined above;

or heteroaryl, heteroarylalkyl, heteroarylalkenyl, heteroarylalkylcarbonyl or heteroarylalkenylcarbonyl, which are substituted by up to three radicals R5 which are independent of one another, and R3 and R4 are identical or different, and independently of one another are hydrogen, alkyl, which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

alkenyl, which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

cycloalkyl, which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

cycloalkenyl, which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl; or aryl, arylalkyl, heteroaryl or heteroarylalkyl, which are substituted by up to five radicals R5 which are independent of one another, in which R5 is as defined above, and R3 and R4 together can also be a radical =C—Z1Z2 linked via a double bond, in which Z1 and Z2 have the meaning given above for R3 and R4, optical isomers thereof, diastereomers in the pure form or in the form of their mixtures and addition salts and prodrugs thereof, with the exception of the compounds in which, simultaneously, R3 and/or R4 are hydrogen and Y is R6 or CR6R7R8.

In a preferred group of compounds of the formula I, Ia, Ib or Ic:

2) n is
zero,
one,
two
or three, the individual substituents R1 independently of one another are fluorine, chlorine, bromine, iodine, trifluoromethyl, trifluoromethoxy, hydroxyl, C1–C8-alkyl, C5–C8-cycloalkyl, C1–C6-alkoxy, (C1–C6-alkoxy)-(C1–C4alkoxy), C1–C6-alkylthio, C1–C6-alkylsulfinyl, C1–C6-alkylsulfonyl, nitro, amino, azido, C1–C6-alkylamino, di(C1–C6-alkyl)amino, piperidino, morpholino, 1-pyrrolidinyl, C1–C6-acyl, C1–C6-acyloxy, C1–C6-acylamino, cyano, carbamoyl, carboxyl, (C1–C6-alkyl)-oxycarbonyl, hydroxysulfonyl or sulfamoyl or a phenyl, phenoxy, phenoxycarbonyl, phenylthio, phenylsulfinyl, phenylsulfonyl, phenoxysulfonyl, phenylsulfonyloxy, phenylsulfonylamino, benzoyl, heteroaroyl, heteroaryl or heteroarylmethyl radical which is optionally substituted by up to three radicals R5 which are independent of one another, in which R5 can be fluorine, chlorine, bromine, iodine, cyano, trifluoromethyl, trifluoromethoxy, nitro, amino, azido, C1–C6alkyl, C3–C8-cycloalkyl, C1–C6-alkoxy, C1–C6-alkylthio, C1–C6-alkylsulfinyl, C1–C6-alkylsulfonyl, C1–C6-alkylamino, di(C1–C6-alkyl)amino, (C1–C6-alkyl)-oxycarbonyl, phenyl, phenoxy or heteroaryl, X is oxygen, sulfur, selenium or substituted nitrogen N—R2 or N—O—R2, in which R2 can have the meanings given below, Y is R6, O—R6, S—R6, N—R6R7, N=CR6R7 or C—R6R7R8, in which R6, R7 and R8 can have the meanings given below, R2, R6, R7 and R8 can be identical or different and, independently of one another, can be hydrogen, C1–C8-alkyl, which is optionally substituted by fluorine, chlorine, bromine, iodine, cyano, amino, mercapto, hydroxyl, C1–C6-acyloxy, benzoyloxy, benzyloxy, phenoxy, C1–C6-alkoxy, Ct-C6-alkylamino, di(C1–C6-alkyl)amino, C1–C6-alkylthio, C1–C6-alkylsulfonyl, phenylsulfonyl, oxo, thioxo, carboxyl or carbamoyl;

C2–C8-alkenyl, which is optionally substituted by fluorine, chlorine, bromine, iodine, cyano, amino, mercapto, hydroxyl, C1–C6-acyloxy, benzoyloxy, benzyloxy, phenoxy, C1–C6-alkoxy, C1–C6-alkylamino, di(C1–C6-alkyl)amino, C1–C6-alkylthio, C1–C6-alkylsulfonyl, phenylsulfonyl, oxo, thioxo, carboxyl or carbamoyl;

C3–C8-alkynyl, which is optionally substituted by fluorine, chlorine, bromine, iodine, cyano, amino, mercapto, hydroxyl, C1–C6-acyloxy, benzoyloxy, benzyloxy, phenoxy, C1–C6-alkoxy, C1–C6-alkylamino, di(C1–C6-alkyl)amino, C1–C6-alkylthio, C1–C6-alkylsulfonyl, phenylsulfonyl, oxo, thioxo, carboxyl or carbamoyl;

C3–C8-cycloalkyl, which is optionally substituted by fluorine, chlorine, bromine, iodine, cyano, amino, mercapto, hydroxyl, C1–C6-acyloxy, benzoyloxy, benzyloxy, phenoxy, C1–C6-alkoxy, C1–C6-alkylamino, di(C1–C6-alkyl)amino, C1–C6-alkylthio, C1–C6-alkylsulfonyl, phenylsulfonyl, oxo, thioxo, carboxyl or carbamoyl;

C5–C8-cycloalkenyl, which is optionally substituted by fluorine, chlorine, bromine, iodine, cyano, amino, mercapto, hydroxyl, C1–C6-acyloxy, benzoyloxy, benzyloxy, phenoxy, C1–C6-alkoxy, C1–C6-alkylamino, di(C1–C6-alkyl)amino, C1–C6-alkylthio, C1–C6-alkylsulfonyl, phenylsulfonyl, oxo, thioxo, carboxyl or carbamoyl;

(C3–C8-cycloalkyl)-(C1–C4-alkyl), which is optionally substituted by fluorine, chlorine, bromine, iodine, cyano, amino, mercapto, hydroxyl, C1–C6-acyloxy, benzoyloxy, benzyloxy, phenoxy, C1–C6-alkoxy, C1–C6-alkylamino, di(C1–C6-alkyl)amino, C1–C6-alkylthio, C1–C6-alkylsulfonyl, phenylsulfonyl, oxo, thioxo, carboxyl or carbamoyl;

(C5–C8-cycloalkenyl)-(C1–C4-alkyl), which is optionally substituted by fluorine, chlorine, bromine, iodine, cyano, amino, mercapto, hydroxyl, C1–C6-acyloxy, benzoyloxy, benzyloxy, phenoxy, C1–C6-alkoxy, C1–C6-alkylamino, di(C1–C6-alkyl)amino, C1–C6-alkylthio, C1–C6-alkylsulfonyl, phenylsulfonyl, oxo, thioxo, carboxyl or carbamoyl;

C1–C6-alkylcarbonyl, which is optionally substituted by fluorine, chlorine, bromine, iodine, cyano, amino, mercapto, hydroxyl, C1–C6-acyloxy, benzoyloxy, benzyloxy, phenoxy, C1–C6-alkoxy, C1–C6-alkylamino, di(C1–C6-alkyl)amino, C1–C6-alkylthio, C1–C6-alkylsulfonyl, phenylsulfonyl, oxo, thioxo, carboxyl or carbamoyl;

C2–C8-alkenylcarbonyl, which is optionally substituted by fluorine, chlorine or hydroxyl, C1–C4-alkoxy, oxo or phenyl;

(C3–C8-cycloalkyl)carbonyl, which is optionally substituted by fluorine, chlorine or hydroxyl, C1–C4-alkoxy, oxo or phenyl;

(C5–C8-cycloalkenyl)carbonyl, which is optionally substituted by fluorine, chlorine or hydroxyl, C1–C4-alkoxy, oxo or phenyl;

(C3–C8-cycloalkyl)-(C1–C3-alkyl)carbonyl, which is optionally substituted by fluorine, chlorine or hydroxyl, C1–C4-alkoxy, oxo or phenyl;

(C5–C6-cycloalkenyl)-(C1–C3-alkyl)carbonyl, which is optionally substituted by fluorine, chlorine or hydroxyl, C1–C4-alkoxy, oxo or phenyl;

C1–C8-alkyloxycarbonyl, which is optionally substituted by fluorine, chlorine, bromine, hydroxyl, C1–C4-alkoxy, C1–C4-alkylamino, di(C1–C4-alkyl)amino, C1–C4-alkylthio; C2–C8-alkenyloxycarbonyl, which is optionally substituted by fluorine, chlorine, hydroxyl, C1–C4-alkoxy, oxo or phenyl;

C2–C8-alkynyloxycarbonyl, which is optionally substituted by fluorine, chlorine, hydroxyl, C1–C4-alkoxy, oxo or phenyl;

C1–C8-alkylthiocarbonyl, which is optionally substituted by fluorine, chlorine, hydroxyl, C1–C4-alkoxy, oxo or phenyl;

C2–C8-alkenylthiocarbonyl, which is optionally substituted by fluorine, chlorine, hydroxyl, C1–C4-alkoxy, oxo or phenyl;

C1–C8-alkylamino- or di(C1–C8-alkyl)aminocarbonyl, which is optionally- substituted by fluorine, chlorine, hydroxyl, C1–C4-alkoxy, oxo or phenyl;

C2–C8-alkenylamino- or di(C2–C6-alkenyl)aminocarbonyl, which is optionally substituted by fluorine, chlorine, hydroxyl, C1–C4-alkoxy, oxo or phenyl;

C1–C6-alkylsulfonyl, which is optionally substituted by fluorine, chlorine, hydroxyl, C1–C4-alkoxy, C1–C4-alkylthio, oxo or phenyl;

C2–C6-alkenylsulfonyl, which is optionally substituted by fluorine, chlorine, hydroxyl, C1–C4-alkoxy, oxo or phenyl;

or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl or arylalkoxycarbonyl, which are substituted by up to three radicals R5, which are independent of one another, and in which the alkyl radical in each case can contain 1 to 5 carbon atoms and R5 is as defined above, or heteroaryl, heteroarylalkyl, heteroarylalkenyl, heteroarylalkylcarbonyl or heteroarylalkenylcarbonyl, which are substituted by up to three radicals R5, which are independent of one another, and in which the alkyl radical in each case can contain 1 to 3 carbon atoms, and R3 and R4 are identical or different, and independently of one another are hydrogen, C1–C8-alkyl, which is optionally substituted by fluorine, chlorine, hydroxyl, amino, mercapto, C1–C4-acyloxy, benzoyloxy, benzyloxy, phenoxy, C1–C4-alkoxy, C1–C4-alkylamino, di(C1–C4-alkyl)amino, C1–C4-alkylthio, C1–C4-alkylsulfonyl, C1–C4alkylsulfinyl, carboxyl or carbamoyl;

C2–C8-alkenyl, which is optionally substituted by fluorine or chlorine, hydroxyl, amino, mercapto, C1–C4acyloxy, benzoyloxy, benzyloxy, phenoxy, C1–C4-alkoxy, C1–C4-alkylamino, di(C1–C4-alkyl)amino, C1–C4-alkylthio, C1–C4-alkylsulfonyl, C1–C4-alkylsulfinyl, carboxyl or carbamoyl;

C3–C8-cycloalkyl, which is optionally substituted by fluorine, chlorine, hydroxyl, amino, mercapto, C1–C4acyloxy, benzoyloxy, benzyloxy, phenoxy, C1–C4-alkoxy, C1–C4-alkylamino, di(C 1 –C4-alkyl)amino, C1–C4-alkylthio, C1–C4-alkylsulfonyl, C1–C4-alkylsulfinyl, carboxyl or carbamoyl;

C3–C8-cycloalkenyl, which is optionally substituted by fluorine or chlorine, hydroxyl, amino, mercapto, C1–C4acyloxy, benzoyloxy, benzyloxy, phenoxy, C1–C4-alkoxy, C1–C4-alkylamino, di(C1–C4-alkyl)amino, C1–C4-alkylthio, C1–C4-alkylsulfonyl, C1–C4-alkylsulfinyl, carboxyl or carbamoyl;

or aryl, arylalkyl, heteroaryl or heteroarylalkyl, which are substituted by up to three radicals R5, which are independent of one another and in which the alkyl radical in each case can contain 1 to 3 carbon atoms, and R5 is as defined above;

R3 and R4 together can also be a radical =C—Z1Z2 linked via a double bond, in which Z1 and Z2 have the meaning given above for R3 and R4.

In another preferred group of compounds of the formula I, Ia, Ib or Ic:

3) n is
  zero,
  one
  or two, the individual substituents R1 independently of one another are fluorine, chlorine, bromine, iodine, trifluoromethyl, trifluoromethoxy, hydroxyl, C1–C6-alkyl, C5–C6-cycloalkyl, C1–C4-alkoxy, (C1–C4-alkoxy)-(C1–C2alkoxy), C1–C4-alkylthio, C1–C4-alkylsulfinyl, C1–C4alkylsulfonyl, nitro, amino, C1–C4-alkylamino, di(C1–C4alkyl)amino, C1–C6-acyl, C1–C4-acyloxy, C1–C4-acylamino, cyano, carbamoyl, carboxyl, (C1–C4-alkyl)-oxycarbonyl or a phenyl, phenoxy, phenoxycarbonyl, phenylthio, phenylsulfinyl, phenylsulfonyl, phenoxysulfonyl, phenylsulfonyloxy, phenylsulfonylamino, benzoyl, heteroaroyl, heteroaryl or heteroarylmethyl radical which is optionally substituted by up to three radicals R5 which are independent of one another, in which R5 can be fluorine, chlorine, trifluoromethyl, trifluoromethoxy, nitro, amino, C1–C4-alkyl, C3–C6-cycloalkyl, C1–C4alkoxy, C1–C4-alkylthio, C1–C4-alkylsulfinyl, C1–C4alkylsulfonyl, C1–C4-alkylamino, di(C1–C4-alkyl)amino, phenyl, phenoxy or heteroaryl, X is oxygen, sulfur or substituted nitrogen N—R2 or N—O—R2, in which R2 can have the meanings given below, Y is R6, O—R6, S—R6, N—R6R7, N=CR6R7 or C—R6R7R8, in which R6, R7 and R8 can have the meanings given below, R2, R6, R7 and R8 can be identical or different and, independently of one another, can be hydrogen, C1–C6-alkyl, which is optionally substituted by fluorine, chlorine, bromine, iodine, cyano, amino, mercapto, hydroxyl, C1–C4-acyloxy, benzoyloxy, benzyloxy, phenoxy, C1–C4-alkoxy, C1–C4-alkylamino, di(C1–C4-alkyl)amino, C1C4-alkylthio, C1–C4-alkylsulfonyl, phenylsulfonyl, oxo, thioxo, carboxyl or carbamoyl;

C2–C6-alkenyl, which is optionally substituted by fluorine, chlorine, cyano, amino, mercapto, hydroxyl, C1–C4-acyloxy, benzoyloxy, benzyloxy, phenoxy, C1–C4alkoxy, C1–C4-alkylamino, di(C1–C4-alkyl)amino, C1–C4alkylthio, C1–C4-alkylsulfonyl, phenylsulfonyl, carboxyl or carbamoyl;

C3–C6-alkynyl, which is optionally substituted by fluorine, chlorine, cyano, amino, mercapto, hydroxyl, C1C4-acyloxy, benzoyloxy, benzyloxy, phenoxy, C1–C4-alkoxy, C1–C4-alkylamino, di(C1–C4-alkyl)amino, C1–C4-alkylthio, C1–C4-alkylsulfonyl, phenylsulfonyl, carboxyl or carbamoyl;

C3–C6-cycloalkyl, which is optionally substituted by fluorine, chlorine, cyano, amino, mercapto, hydroxyl, C1C4-acyloxy, benzoyloxy, benzyloxy, phenoxy, C1–C4-alkoxy, C1–C4-alkylamino, di(C1–C4-alkyl)amino, C1–C4-alkylthio, C1–C4-alkylsulfonyl, phenylsulfonyl, carboxyl or carbamoyl;

C5–C6-cycloalkenyl, which is optionally substituted by fluorine, chlorine, cyano, amino, mercapto, hydroxyl, C1C4-acyloxy, benzoyloxy, benzyloxy, phenoxy, C1–C4-alkoxy, C1–C4-alkylamino, di(C1–C4-alkyl)amino, C1–C4-alkylthio, C1–C4-alkylsulfonyl, phenylsulfonyl, carboxyl or carbamoyl;

(C3–C6-cycloalkyl)-(C1–C2-alkyl), which is optionally substituted by fluorine, chlorine, cyano, amino, mercapto, hydroxyl, C1–C4-acyloxy, benzoyloxy, benzyloxy, phenoxy, C1–C4-alkoxy, C1–C4-alkylamino, di(C1–C4-alkyl)amino, C1–C4-alkylthio, C1–C4-alkylsulfonyl, phenylsulfonyl, carboxyl or carbamoyl;

(C5–C6-cycloalkenyl)-(C1–C2-alkyl), which is optionally substituted by fluorine, chlorine, cyano, amino, mercapto, hydroxyl, C1–C4-acyloxy, benzoyloxy, benzyloxy, phenoxy, C1–C4-alkoxy, C1–C4-alkylamino, di(C1–C4-alkyl)amino, C1–C4-alkylthio, C1–C4-alkylsulfonyl, phenylsulfonyl, carboxyl or carbamoyl;

C1–C6-alkylcarbonyl, which is optionally substituted by fluorine, chlorine, cyano, amino, mercapto, hydroxyl, C1C4-acyloxy, benzoyloxy, benzyloxy, phenoxy, C1–C4-alkoxy, C1–C4-alkylamino, di(C1–C4-alkyl)amino, C1–C4-alkylthio, C1–C4-alkylsulfonyl, carboxyl or carbamoyl;

C2–C6-alkenylcarbonyl, which is optionally substituted by
hydroxyl, C1–C4-alkoxy, oxo or fluorine, chlorine, phenyl;

(C3–C6-cycloalkyl)carbonyl, which is optionally substituted by fluorine, chlorine, hydroxyl, C1–C4-alkoxy, oxo or phenyl;

(C5–C6-cycloalkenyl)carbonyl, which is optionally substituted by fluorine, chlorine, hydroxyl, C1–C4-alkoxy, oxo or phenyl;

(C3–C6-cycloalkyl)-(C1–C2-alkyl)carbonyl, which is optionally substituted by fluorine, chlorine, hydroxyl, C1–C4-alkoxy, oxo or phenyl;

(C5–C6-cycloalkenyl)-(C1–C2-alkyl)carbonyl, which is optionally substituted by fluorine, chlorine, hydroxyl, C1–C4-alkoxy, oxo or phenyl;

C1–C6-alkyloxycarbonyl, which is optionally substituted by fluorine, chlorine, C1–C4-alkoxy, C1–C4-alkylamino, di(C1–C4-alkyl)amino or C1–C4-alkylthio;

C2–C6-alkenyloxycarbonyl, which is optionally substituted by fluorine, chlorine, C1–C4-alkoxy or phenyl;

C2–C6-alkynyloxycarbonyl, which is optionally substituted by fluorine, chlorine, C1–C4-alkoxy or phenyl;

C1–C6-alkylthiocarbonyl, which is optionally substituted by fluorine, chlorine, C1–C4-alkoxy or phenyl;

C2–C6-alkenylthiocarbonyl, which is optionally substituted by fluorine, chlorine, C1–C4-alkoxy or phenyl;

C1–C6-alkylamino- or di(C1–C6-alkyl)aminocarbonyl, which is optionally substituted by fluorine, chlorine, C1–C4alkoxy or phenyl;

C2–C6-alkenylamino- or di(C2–C6-alkenyl)aminocarbonyl, which is optionally substituted by fluorine, chlorine, C1–C4-alkoxy or phenyl;

C1–C6-alkylsulfonyl, which is optionally substituted by fluorine, chlorine, C1–C4-alkoxy or phenyl;

C2–C6-alkenylsulfonyl, or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl or arylalkoxycarbonyl, which are substituted by up to three radicals R5, which are independent of one another, and in which the alkyl radical in each case can contain 1 to 4 carbon atoms and R5 is as defined above, or heteroaryl, heteroarylalkyl, heteroarylalkenyl, heteroarylalkylcarbonyl or heteroarylalkenylcarbonyl, which are substituted by up to three radicals R5, which are independent of one another, and in which the alkyl radical in each case can contain 1 to 3 carbon atoms, and R3 and R4 are identical or different and independently of one another are hydrogen, C1–C6-alkyl, which is optionally substituted by fluorine, chlorine, hydroxyl, amino, mercapto, C1–C4-acyloxy, benzoyloxy, benzyloxy, phenoxy, C1–C4-alkoxy, C1–C4-alkylamino, di(C1–C4-alkyl)amino, C1–C4-alkylthio, C1–C4-alkylsulfonyl, C1–C4-alkylsulfinyl, carboxyl or carbamoyl;

C2–C6-alkenyl, which is optionally substituted by fluorine or chlorine, phenoxy, C1–C4-alkoxy, C1–C4alkylthio, C1–C4-alkylsulfonyl or C1–C4-alkylsulfinyl;

C3–C6-cycloalkyl, which is optionally substituted by fluorine, chlorine, hydroxyl, amino, mercapto, C1–C4acyloxy, benzoyloxy, benzyloxy, phenoxy, C1–C4-alkoxy, C1–C4-alkylamino, di(C1–C4-alkyl)amino, C1–C4-alkylthio, C1–C4-alkylsulfonyl or C1–C4-alkylsulfinyl;

C3–C6-cycloalkenyl, which is optionally substituted by fluorine or chlorine, phenoxy, C1–C4-alkoxy, C1–C4alkylthio, C1–C4-alkylsulfonyl or C1–C4-alkylsulfinyl;

or aryl, arylalkyl, heteroaryl or heteroarylalkyl, which are substituted by up to three radicals R5, which are independent of one another, and in which the alkyl radical in each case can contain I to 3 carbon atoms and R5 is as defined above, and one of the radicals R3 or R4 can be hydrogen, or R3 and R4 together can also be a radical =C—Z1Z2 linked via a double bond, in which Z1 and Z2 have the meaning given above for R3 and R4.

In another preferred group of compounds of the formula I, Ia, Ib or Ic:

4) n is
zero,
one
or two, the individual substituents R1 independently of one another are fluorine, chlorine, bromine, trifluoromethyl, trifluoromethoxy, hydroxyl, C1–C4-alkyl, C1–C4-alkoxy, (C1–C4-alkoxy)-(C1–C2-alkoxy), C1–C4-alkylthio, C1–C4alkylsulfinyl, C1–C4-alkylsulfonyl, nitro, amino, C1–C4alkylamino, di(C1–C4-alkyl)amino, C1–C4-acyl, C1–C4acyloxy, C1–C4-acylamino, cyano, carbamoyl, carboxyl, (C1–C4-alkyl)-oxycarbonyl or a phenyl, phenoxy, phenoxycarbonyl, phenylthio, phenylsulfinyl, phenylsulfonyl, benzoyl, heteroaroyl, heteroaryl or heteroarylmethyl radical, which is optionally substituted by up to three radicals R5 which are independent of one another, in which R5 can be fluorine, chlorine, trifluoromethyl, trifluoromethoxy, nitro, amino, C1–C4-alkyl, C1–C4-alkoxy, C1–C4-alkylthio, C1–C4-alkylsulfinyl, C1–C4-alkylsulfonyl, C1–C4-alkylamino, di(C1–C4-alkyl)amino, phenyl or phenoxy, X is oxygen, sulfur or substituted nitrogen N—R2 or N—O—R2, in which R2 can have the meanings given below, Y is O—R6, S—R6, N—R6R7 or N=CR6R7, in which R6, R7 and R8 can have the meanings given below, R2, R6, R7 and R8 can be identical or different and, independently of one another, can be hydrogen, C1–C6-alkyl, which is optionally substituted by fluorine, chlorine, amino, mercapto, hydroxyl, C1–C4-acyloxy, benzoyloxy, benzyloxy, phenoxy, C1–C4-alkoxy, C1–C4-alkylamino, di(C1–C4-alkyl)amino or C1–C4-alkylthio;

C2–C6-alkenyl, which is optionally substituted by fluorine, chlorine, amino, mercapto, hydroxyl, C1–C4acyloxy, benzoyloxy, benzyloxy, phenoxy, C1–C4-alkoxy, C1–C4-alkylamino, di(C1–C4-alkyl)amino or C1–C4-alkylthio;

C3–C6-alkynyl, which is optionally substituted by fluorine, chlorine, amino, mercapto, hydroxyl, C1–C4acyloxy, benzoyloxy, benzyloxy, phenoxy, C1–C4-alkoxy, C1–C4-alkylamino, di(C1–C4-alkyl)amino or C1–C4-alkylthio;

C3–C6-cycloalkyl, which is optionally substituted by fluorine, chlorine, C1–C4-acyloxy, benzoyloxy, phenoxy, C1–C4-alkoxy, C1–C4-alkylamino, di(C1–C4-alkyl)amino or C1–C4-alkylthio;

C5–C6-cycloalkenyl, (C3–C6-cycloalkyl)-(C1–C2-alkyl), (C5–C6-cycloalkenyl)-(C1–C2-alkyl), C1–C6-alkylcarbonyl, which is optionally substituted by fluorine, chlorine, amino, mercapto, hydroxyl, C1–C4acyloxy, benzoyloxy, benzyloxy, phenoxy, C1–C4-alkoxy, C1–C4-alkylamino, di(C1–C4-alkyl)amino or thio;

C2–C4-alkenylcarbonyl, (C3–C6-cycloalkyl)carbonyl, (C5–C6-cycloalkenyl)carbonyl, (C3–C6-cycloalkyl)-(C1–C2-alkyl)carbonyl, (C5–C6-cycloalkenyl)-(C1–C2-alkyl)carbonyl, C1–C6-alkyloxycarbonyl, which is optionally substituted by fluorine, chlorine, C1–C4-alkoxy, C1–C4-alkylamino, di(C1–C4-alkyl)amino or C1–C4-alkylthio;

C2–C6-alkenyloxycarbonyl,

C2–C6-alkynyloxycarbonyl,

C1–C6-alkylthiocarbonyl,

C2–C6-alkenylthiocarbonyl,

C1–C6-alkylamino- or di (C1–C6-alkyl)aminocarbonyl,

C2–C6-alkenylamino- or di(C2–C4-alkenyl)aminocarbonyl,

C1–C6-alkylsulfonyl,
C2–C6-alkenylsulfonyl, or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl or arylalkoxycarbonyl, which are substituted by up to two radicals R5, which are independent of one another, and in which the alkyl radical in each case can contain 1 to 3 carbon atoms and R5 is as defined above, or heteroaryl, heteroarylalkyl, heteroarylalkenyl, heteroarylalkylcarbonyl or heteroarylalkenylcarbonyl, which are substituted by up to two radicals R5, which are independent of one another, and in which the alkyl radical in each case can contain 1 or 2 carbon atoms, and R3 and R4 are identical or different and independently of one another are C1–C6-alkyl, which is optionally substituted by fluorine, chlorine, hydroxyl, amino, mercapto, C1–C4-acyloxy, benzoyloxy, benzyloxy, phenoxy, C1–C4alkoxy, C1–C4-alkylamino, di(C1–C4-alkyl)amino, C1–C4alkylthio, C1–C4-alkylsulfonyl, C1–C4-alkylsulfinyl or carboxyl;

C2–C6-alkenyl, which optionally substituted by fluorine or chlorine;

C3–C6-cycloalkyl, C5–C6-cycloalkenyl, which is optionally substituted by fluorine or chlorine;

or aryl, arylalkyl, heteroaryl or heteroarylalkyl, which are substituted by up to three radicals R5, which are independent of one another, and in which the alkyl radical in each case can contain 1 or 2 carbon atoms and R5 is as defined above, one of the radicals R3 or R4 can also be hydrogen, and R3 and R4 together can also be a radical =C—Z1Z2 linked via a double bond, in which Z1 and Z2 have the meaning given above for R3 and R4.

The present invention furthermore relates to the use of compounds of the formula I

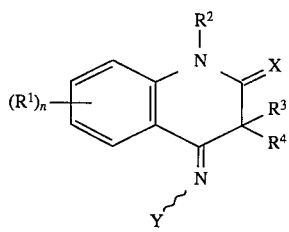

(I)

and tautomeric forms thereof, of the formula Ia

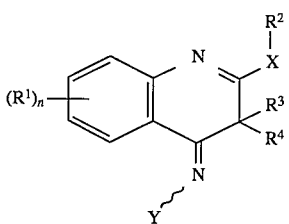

(Ia)

Ib and Ic

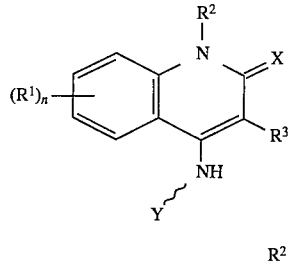

(Ib)

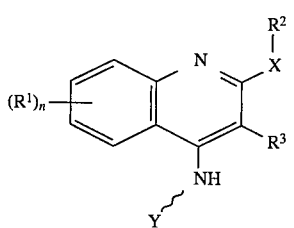

(Ic)

in which:

n is
zero,
one,
two,
three
or four, the individual substituents R1 independently of one another are fluorine, chlorine, bromine, iodine, trifluoromethyl, trifluoromethoxy, hydroxyl, alkyl, cycloalkyl, alkoxy, alkoxy(alkoxy), alkylthio, alkylsulfinyl, alkylsulfonyl, nitro, amino, azido, alkylamino, dialkylamino, piperidino, morpholino, 1-pyrrolidinyl, acyl, acyloxy, acylamino, cyano, carbamoyl, carboxyl, alkyloxycarbonyl, hydroxysulfonyl or sulfamoyl or a phenyl, phenoxy, phenoxycarbonyl, phenylthio, phenylsulfinyl, phenylsulfonyl, phenoxysulfonyl, phenylsulfonyloxy, anilinosulfonyl, phenylsulfonylamino, benzoyl, heteroaroyl, heteroaryl or heteroarylmethyl radical which is optionally substituted by up to five radicals R5 which are independent of one another, in which R5 can be fluorine, chlorine, bromine, iodine, cyano, trifluoromethyl, trifluoromethoxy, nitro, amino, azido, alkyl, cycloalkyl, alkoxy, alkylthio, alkylsulfinyl, alkylsulfonyl, alkylamino, dialkylamino, alkyloxycarbonyl, phenyl, phenoxy or heteroaryl, X is oxygen, sulfur, selenium or substituted nitrogen N—R2 or N—O—R2, in which R2 can have the meanings given below, Y is R6, O—R6, S—R6, N—R6R7, N=C—R6R7 or C—R6R7R8, in which R6, R7 and R8 can have the meanings given below, R2, R6, R7 and R8 can be identical or different and can be, independently of one another, hydrogen, alkyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkenyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkynyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkenyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkyl)-(alkyl), which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkenyl)-(alkyl), which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkylcarbonyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkenylcarbonyl, which is optionally substituted by fluorine, chlorine or hydroxyl, alkoxy, oxo or phenyl;

(cycloalkyl)carbonyl, which is optionally substituted by fluorine, chlorine or hydroxyl, alkoxy, oxo or phenyl;

(cycloalkenyl)carbonyl, which is optionally substituted by fluorine, chlorine or hydroxyl, alkoxy, oxo or phenyl;

(cycloalkyl)-(alkyl)carbonyl, which is optionally substituted by fluorine, chlorine or hydroxyl, alkoxy, oxo or phenyl;

(cycloalkenyl)-(alkyl)carbonyl, which is optionally substituted by fluorine, chlorine or hydroxyl, alkoxy, oxo or phenyl;

alkyloxycarbonyl, which is optionally substituted by fluorine, chlorine, bromine, hydroxyl, alkoxy, alkylamino, dialkylamino or alkylthio;

alkenyloxycarbonyl, which is optionally substituted by fluorine, chlorine, hydroxyl, alkoxy, oxo or phenyl;

alkynyloxycarbonyl, which is optionally substituted by fluorine, chlorine, hydroxyl, alkoxy, oxo or phenyl;

alkylthiocarbonyl, which is optionally substituted by fluorine, chlorine, hydroxyl, alkoxy, oxo or phenyl;

alkenylthiocarbonyl, which is optionally substituted by fluorine, chlorine, hydroxyl, alkoxy, oxo or phenyl;

alkylamino- or dialkylaminocarbonyl, which is optionally substituted by fluorine, chlorine, hydroxyl, alkoxy, oxo or phenyl;

alkenylamino- or dialkenylaminocarbonyl, which is optionally substituted by fluorine, chlorine, hydroxyl, alkoxy, oxo or phenyl;

alkylsulfonyl, which is optionally substituted by fluorine, chlorine, hydroxyl, alkoxy, alkylthio, oxo or phenyl;

alkenylsulfonyl, which is optionally substituted by fluorine, chlorine, hydroxyl, alkoxy, oxo or phenyl;

or aryl, arylcarbonyl, aryl(thiocarbonyl), (arylthio)carbonyl, (arylthio)thiocarbonyl, aryloxycarbonyl, (arylamino)thiocarbonyl, arylsulfonyl, arylalkyl, arylalkenyl, arylalkynyl, arylalkylcarbonyl, arylalkenylcarbonyl or arylalkoxycarbonyl, which are substituted by up to five radicals R5 which are independent of one another, in which R5 is as defined above;

or heteroaryl, heteroarylalkyl, heteroarylalkenyl, heteroarylalkylcarbonyl or heteroarylalkenylcarbonyl, which are substituted by up to three radicals R5 which are independent of one another, and R3 and R4 are identical or different and independently of one another are hydrogen, alkyl, which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

alkenyl, which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

cycloalkyl, which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

cycloalkenyl, which is optionally substituted by fluorine or chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

or aryl, arylalkyl, heteroaryl or heteroarylalkyl, which are substituted by up to five radicals R5 which are independent of one another, in which R5 is as defined above, and R3 and R4 together can also be a radical =C—Z1Z2 linked via a double bond, in which Z1 and Z2 have the meaning given above for R3 and R4, and R3 and R4, or R3 and Y furthermore can also be part of a saturated or unsaturated carbo- or heterocyclic ring, which can optionally be substituted by fluorine, chlorine, hydroxyl, amino, alkyl, alkenyl, alkynyl, acyloxy, benzoyloxy, alkoxy, alkylthio, oxo, thioxo, carboxyl, carbamoyl or phenyl, optical isomers thereof, diastereomers in the pure form or in the form of their mixtures and addition salts and prodrugs thereof, for use as medicaments.

The compounds mentioned above under 1)–4) are preferred for the use according to the invention.

The alkyl groups mentioned in the preceding definitions can be straight-chain or branched. Unless defined otherwise, they preferably contain 1–8, particularly preferably 1–6, especially 1–4 carbon atoms. Examples are the methyl, ethyl, propyl, 1-methylethyl, butyl, 1-methylpropyl, 2-methylpropyl and 1,1-dimethylethyl group and the like.

The alkenyl groups mentioned in the preceding definitions can be straight-chain or branched and contain 1 to 3 double bonds. Unless defined otherwise, these groups preferably contain 2–8, in particular 2–6 carbon atoms. Examples are the 2-propenyl, 1-methylethenyl, 2-butenyl, 3-butenyl, 2-methyl-2-propenyl, 3-methyl-2-butenyl, 2,3-dimethyl-2-butenyl, 3,3-dichloro-2-propenyl and pentadienyl The alkynyl groups mentioned in the preceding definitions can be straight-chain or branched and contain 1 to 3 triple bonds. Unless defined otherwise, they preferably contain 2–8, particularly preferably 3–6 carbon atoms.

Examples are the 2-propynyl and 3-butynyl group and the like.

The cycloalkyl and cycloalkenyl groups mentioned in the preceding definitions, unless defined otherwise, contain preferably 3–8, particularly preferably 4–6 carbon atoms.

Examples are the cyclopropyl, cyclobutyl, cyclopentyl, cyclopentenyl, cyclohexyl or cyclohexenyl group.

The acyl groups mentioned in the preceding definitions can be aliphatic, cycloaliphatic or aromatic. Unless defined otherwise, they contain preferably 1–8, particularly preferably 2–7 carbon atoms. Examples of acyl groups are the formyl, acetyl, chloroacetyl, trifluoroacetyl, hydroxyacetyl, glycyl, propionyl, butyryl, isobutyryl, pivaloyl, cyclohexanoyl or benzoyl group. Groups which are suitable for the aryl groups mentioned in the preceding definitions are preferably aromatic groups having 6–14 carbon atoms, in particular having 6–10 carbon atoms, such as, for example, phenyl and naphthyl.

Possible hetero atoms in the abovementioned heterocyclic rings and heteroaryl groups are, in particular, for example O, S and N, and in the case of an N-containing ring which is saturated at this point, N—Z is present, in which Z is H or R2 having the particular definitions described above.

Unless defined otherwise, the heterocyclic rings preferably have 1–15 carbon atoms and 1–6 hetero atoms, in particular 3–11 carbon atoms and 1–4 hetero atoms. For the heterocyclic rings and heteroaryl groups mentioned in the preceding definitions, thiophene, furan, pyridine, pyrimidine, indole, quinoline, isoquinoline, oxazole, isoxazole, thiazole or isothiazole, for example, are possible.

These definitions similarly apply to heteroaryl in the heteroarylmethyl radical.

The aralkyl groups mentioned in the preceding definitions are, for example, benzyl, phenylethyl, naphthylmethyl or styryl.

The abovementioned substituents R1 to R8 are preferably trisubstituted, particularly preferably disubstituted, and especially monosubstituted, by the particular substituents mentioned.

For the particular composite substituent definitions (such as, for example, aryloxycarbonyl), the ranges described above as preferred are likewise preferred for the individual substituents.

Compounds of the formulae I, Ia, Ib and Ic can have several asymmetric carbon atoms, depending on the various substituents.

The invention therefore relates both to the pure stereoisomers and to mixtures thereof, such as, for example, the associated racemate.

The pure stereoisomers of the compounds of the formulae I, Ia, Ib and Ic can be prepared directly or separated subsequently by known methods or by methods analogous to known methods.

The present invention furthermore relates to a process for the preparation of compounds of the formulae I, Ia, Ib and Ic as described above under 1)–4), which comprises A) for the preparation of compounds of the formulae I and Ib, where X is oxygen, and Ia and Ic, where X is as defined under 1)–4)—with the exception of N—R2 being N—H—Y is R6, O—R6, S—R6, N—R6R7, N═C—R6R7 or C—R6R7R8 and the radicals R1, R2, R3, R4, R5, R6, R7 and R8 are as defined under 1)–4), reacting a compound of the formula II, IIa, IIb or IIc

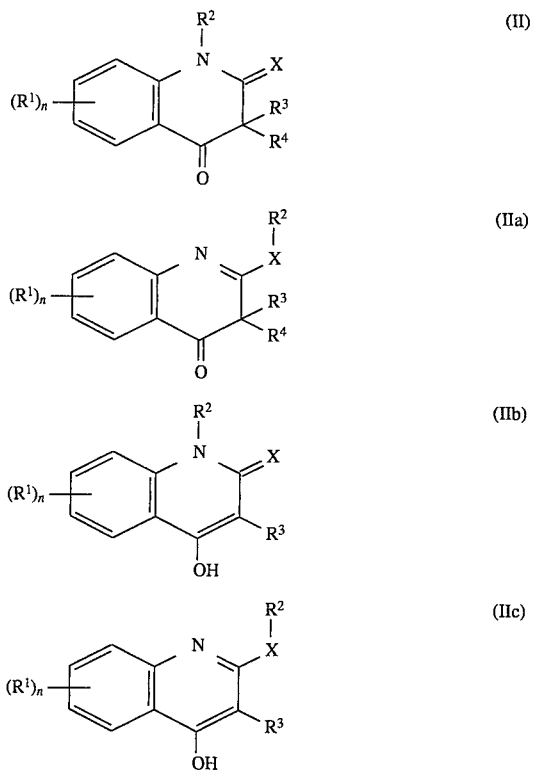

in which the definitions mentioned under 1)–4) apply to R1, R2, R3, R4 and R5,
with a compound of the formula III

Y—NH₂    (III)

in which Y can be R6, O—R6, S—R6, N—R6R7, N═C—R6R7 or C—R6R7R8 and the definitions mentioned under 1)–4) apply to R6, R7 and R8,
or B) preparing compounds of the formulae I, Ia, Ib and Ic, where X, Y and the radicals R1, R2, R3, R4, R5, R6, R7 and R8 are as defined under 1)–4), by reaction of a compound of the formula I, Ia, Ib or Ic, in which the definitions mentioned under 1)–4) apply to X and the radicals R1, R2, R3, R4, R5 and R6 and Y is H, OH, SH, NH₂ or NHR6, with a reagent of the formula IV

R9—Z    (IV)

in which R9 has the meanings mentioned above under 1)–4) for R2, R6, R7 and R8, with the exception of hydrogen, and Z is a leaving group, or C) preparing compounds of the formulae I and Ib, where X is sulfur and R1, R2, R3, R4, R5, R6, R7 and R8 are as defined under 1)–4), by reaction of a compound of the formula I or Ib, in which X is oxygen and the definitions mentioned under 1)–4) apply to R1, R2, R3, R4, R5, R6, R7 and R8, with a sulfurizing reagent,
or D) for the preparation of compounds of the formulae I, Ia, Ib and Ic, where X and R1, R2, R3, R4 and R5 are as defined under 1)–4) and Y is O—R6, S—R6 or N—6R7, reacting compounds of the formulae I, Ia, Ib or Ic, where X and R1, R2, R3, R4 and R5 are as defined under 1)–4) and Y is OH, SH, NH$_2$ or NHR6, with a compound of the formula V $$R9-OH \quad (V)$$

in which R9 can be alkyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkenyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkynyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

cycloalkenyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkyl)-(alkyl), which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkenyl)-(alkyl), which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkylcarbonyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkenylcarbonyl, which is optionally substituted by fluorine, chlorine or hydroxyl, alkoxy, oxo or phenyl; (cycloalkyl)carbonyl, which is optionally substituted by fluorine, chlorine or hydroxyl, alkoxy, oxo or phenyl; (cycloalkenyl)carbonyl, which is optionally substituted by fluorine, chlorine or hydroxyl, alkoxy, oxo or phenyl; (cycloalkyl)-(alkyl)carbonyl, which is optionally substituted by fluorine, chlorine or hydroxyl, alkoxy, oxo or phenyl;

(cycloalkenyl)-(alkyl)carbonyl, which is optionally substituted by fluorine, chlorine or hydroxyl, alkoxy, oxo or phenyl;

or aryl, arylcarbonyl, arylalkyl, arylalkenyl, arylalkynyl, arylalkylcarbonyl or arylalkenylcarbonyl, which are substituted by up to five radicals R5 which are independent of one another, in which R5 is as defined above, or heteroaryl, heteroarylalkyl, heteroarylalkenyl, heteroarylalkylcarbonyl or heteroarylalkenylcarbonyl, which are substituted by up to three radicals R5 which are independent of one another, in the presence of a dehydrating agent, or E) preparing compounds of the formulae I and Ib, where X is oxygen and Y, R1, R2, R3, R4 and R5 are as defined under 1)–4), by cyclization of a compound of the formula VI

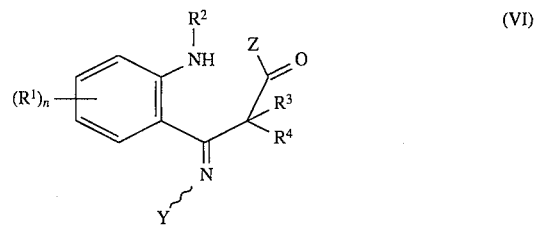

where Y, R1, R2, R3, R4 and R5 ace as defined under 1)–4) and Z is a leaving group.

The abovementioned method A preferably proceeds under the following conditions:

The reaction is advantageously carried out in a solvent. Suitable solvents are, for example, aromatic hydrocarbons, such as toluene or xylene, water, lower alcohols, such as methanol, ethanol, methylglycol or 1-butanol, ethers, such as tetrahydrofuran or glycol dimethyl ether, basic solvents, such as pyridine or N-methylimidazole, carboxylic acids, such as acetic acid, or mixtures of these solvents. The presence of a suitable acid or basic catalyst, for example p-toluenesulfonic acid, acetic acid, mineral acids or salts, such as sodium acetate, sodium carbonate, potassium carbonate or pyridinium hydrochloride, is advantageous. The reaction temperature can be between 0° and 200° C., and is preferably at the boiling point of the solvent.

The abovementioned method B preferably proceeds under the following conditions:

The substituent Z in the formula IV is a suitable leaving group, such as, for example, chlorine, bromine or iodine, a suitable radical of sulfuric acid, an aliphatic or aromatic sulfonic acid ester or optionally halogenated acyloxy.

The reaction is advantageously carried out in a solvent in the presence of a suitable base to trap the acid liberated during the reaction.

Solvents which can be used are aromatic hydrocarbons, such as toluene or xylene, lower alcohols, such as methanol, ethanol, methylglycol or 1-butanol, ethers, such as tetrahydrofuran or glycol dimethyl ether, dipolar aprotic solvents, such as N,N-dimethylformamide, N-methylpyrrolidone, acetonitrile, nitrobenzene or dimethyl sulfoxide, or mixtures of these solvents.

Suitable bases are, for example, alkali metal or alkaline earth metal carbonates or bicarbonates, such as sodium bicarbonate, sodium carbonate or calcium carbonate, alkali metal or alkaline earth metal hydroxides, such as potassium hydroxide or barium hydroxide, alcoholares, such as sodium ethanolate or potassium tert-butylate, organolithium compounds, such as butyllithium or lithium diisopropylamide, alkali metal or alkaline earth metal hydrides, such as sodium hydride or calcium hydride, alkali metal fluorides, such as potassium fluoride, or an organic base, such as triethylamine or pyridine.

Two-phase systems with aqueous solutions of bases in the presence of a phase transfer catalyst, such as, for example, benzyltriethylammonium chloride, are also possible. In some cases, the addition of an iodine salt, for example lithium iodide, is appropriate. The reaction is usually carried out at temperatures between −10° and 160° C., preferably at room temperature or the boiling point of the solvent.

For this reaction, any nucleophilic substituents, such as, for example, hydroxyl, mercapto or amino groups, must be derivatized in a suitable manner or provided with the customary protective groups which can be split off again, such as, for example, acetyl or benzyl, before the reaction is carried out.

For the reaction as described above under C), 2,4-bis(4-methoxyphenyl)-1,3-dithia-2,4-diphosphetane 2,4-disulfide (Lawesson reagent), bis(tricyclohexyltin) sulfide, bis(tri-n-butyltin) sulfide, bis(triphenyltin) sulfide, bis(trimethylsilyl) sulfide or phosphorus pentasulfide is preferably used as the sulfurizing reagent. The reaction is advantageously carried out in an organic solvent or a solvent mixture, at room temperature or higher, preferably at the boiling point of the reaction mixture, and if possible under anhydrous conditions. Carbon disulfide, toluene, xylene, pyridine or 1,2-dichloroethane, for example are suitable. If the tin sulfides or silyl sulfides mentioned are used, it is appropriate to carry out the sulfurization reaction in the presence of a Lewis acid, such as boron trichloride.

If other carbonyl groups are present, these are to be protected, if appropriate, before the sulfurization reaction, by a suitable protective group by known methods, for example by acetalization.

Dehydrating systems, such as azodicarboxylic acid dialkyl esters and a trialkyl- or triarylphosphine, are required for the reaction described above under D).

Suitable solvents for this reaction are halogenated solvents, such as methylene chloride or 1,2-dichloroethane, ethers, such as tetrahydrofuran or 1,2-dimethoxyethane, aromatic hydrocarbons, such as toluene or xylene, or mixtures of these solvents.

The reaction should be carried out under anhydrous conditions.

The reaction is preferably carried out at temperatures between 0° and 100° C., particularly preferably at room temperature.

The cyclization described under E) is carried out in a suitable solvent, such as lower alcohols, for example methanol, ethanol or methylglycol, ethers, for example tetrahydrofuran or 1,2-dimethoxyethane, or dipolar aprotic solvents, for example N,N-dimethylformamide or N-methylpyrrolidone, in the presence of a base; suitable bases are alkali metal or alkaline earth metal carbonates or bicarbonates, such as sodium carbonate, calcium carbonate or sodium bicarbonate, alkali metal or alkaline earth metal hydroxide, such as potassium hydroxide or barium hydroxide, alcoholates, such as sodium ethanolate or potassium tert-butylate, organolithium compounds, such as butyllithium or lithium diisopropylamide, alkali metal or alkaline earth metal hydrides, such as sodium hydride or calcium hydride, or an organic base, such as triethylamine or pyridine—the latter can also be used as solvents—or organic or inorganic acids, such as acetic acid, trifluoroacetic acid, hydrochloric acid or phosphoric acid.

The reaction is preferably carried out at temperatures between −10° and 120° C., particularly preferably at room temperature.

The substituent Z in the formula VI is hydroxyl, alkoxy, chlorine, bromine or iodine, or optionally halogenated acyloxy.

The starting materials of the formulae II, IIa, IIb or IIc are known from the literature or can be prepared by methods which are described in the literature (cf., for example, A. B. Daruwala et al., J. Med. Chem. 1974, 17, 819, G. M. Coppola, Synthesis 1980, 505 and literature cited here).

Another process for the preparation of compounds of the formulae II or IIb, where X is oxygen and R1, R2, R3, R4 and R5 are as defined under 1)–4), is the cyclization of a compound of the formula VII

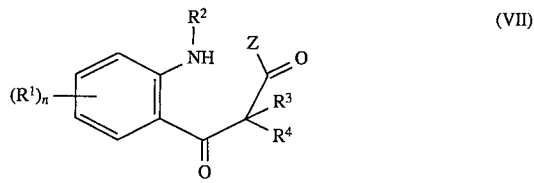

in which R1, R2, R3, R4 and R5 are as defined under 1)–4) and Z is a leaving group. The reaction is carried out as described under E). Compounds of the formula VI are obtained, for example, by reaction of compounds of the formula VII with compounds of the formula III under the conditions described under A). The definitions mentioned under A) for the substituents Y, R1, R2, R3, R4, R5, R6, R7 and R8 apply to the compounds of the formulae VI, VII and III.

Compounds of the formula VII are known from the literature or can be prepared by methods which are described in the literature (cf., for example, Methoden der Organischen Chemie (Methods of Organic Chemistry) (Houben-Weyl), E. Müller (editor); G. Thieme Verlag, Stuttgart, 1957; Volume VIII, page 560 et seq.).

The medicaments according to the invention can be used enterally (orally), parenterally (intravenously), rectally, subcutaneously, intramuscularly or locally (topically). They can be administered in the form of solutions, powders (tablets or capsules, including microcapsules), ointments (creams or gels) or suppositories. Possible auxiliaries for such formulations are the pharmaceutically customary liquid or solid fillers and extenders, solvents, emulsifiers, lubricants, flavor correctants, dyestuffs and/or buffer substances. 0.1–10 , preferably 0.2–8 mg/kg of body weight are administered once or several times daily as an expedient dosage.

The dosage units used expediently depend on the particular pharmacokinetics of the substance used or of the pharmaceutical formulation used.

The dosage unit used for the compounds according to the invention is, for example, 1–1500 mg, preferably 50–500 mg.

The compounds according to the invention can also be administered in combination with other antiviral agents, such as, for example, nucleoside analogs, protease inhibitors or adsorption inhibitors and immunostimulants, interferons, interleukins and colony-stimulating factors (for example GM-CSF, G-CSF or M-CSF).

Activity tests
Testing of preparations against HIV in a cell culture
Description of the method
Medium:
RPMI pH 6.8
The complete medium additionally contains 20% of fetal calf serum and 40 IU/ml of recombinant interleukin 2. Cells:
Lymphocytes isolated from fresh donor blood by means of Ficol® gradient centrifugation are cultured, with addition of 2 mg/ml of phytohemagglutinin (Wellcome) in the complete medium at 37° C. under 5% of $CO_2$ for 36 hours. After addition of 10% of dimethyl sulfoxide, the cells are frozen at a cell density of $5\times10^6$ and stored in liquid nitrogen. For the experiment, the cells are thawed, washed in RPMI medium and cultured in the complete medium for 3–4 days.

Procedure:

The test preparations were dissolved in dimethyl sulfoxide in a concentration of 16.7 mg/ml and diluted to 1 mg/ml in complete medium.

0.4 ml of medium was initially introduced into 24-well multiwell dishes. After addition of 0.1 ml of the dissolved preparation into the upper row of the dish, a geometric dilution series was produced by transferring in each case 0.1 ml. Preparation-free controls always contained 0.4 ml of complete medium with 0.5% of dimethyl sulfoxide.

Lymphocyte cultures having a cell count of $5 \times 10^5$ cells/ml were infected by addition of $\frac{1}{50}$ of the volume of supernatant from HIV-infected lymphocyte cultures. The titer of these culture supernatants was determined by end point dilution with $1-5 \times 10^6$ infectious units/ml. After incubation at 37° C. for 30 minutes, the infected lymphocytes were centrifuged off and taken up again in the same volume of medium. In each case 0.6 ml of this cell suspension was introduced into each of the depression walls of the test plate. The batches were incubated at 37° C. for 3 days.

Evaluation:

The infected cell cultures were examined under the microscope for the presence of giant cells, which indicate active multiplication of the virus in the culture. The lowest concentration of preparation at which no giant cells occurred was determined as the inhibitory concentration against HIV. As a control, the supernatants from the culture plates were investigated for the presence of the HIV antigen with the aid of an HIV antigen test in accordance with the manufacturer's information (Organon).

Results:

Table 1 shows the results of this test.

TABLE 1

| Compound of Example No. | T-Cell culture assay Minimum inhibitory concentration (µg/ml) |
|---|---|
| 2 | 0.2 |
| 3 | 0.008 |
| 6 | 0.008 |
| 7 | 0.008 |
| 8 | 0.2 |
| 9 | 0.04 |
| 32 | 1.0 |
| 33 | 0.2 |
| 39 | 1.0 |
| 48 | 0.04 |
| 50 | 0.2 |
| 62 | 0.04 |
| 67 | 0.04 |
| 82 | <0.08 |
| 87 | 0.04 |
| 103 | 0.04 |
| 104 | 0.04 |
| 115 | 0.04 |
| 119 | 0.008 |
| 122 | 0.008 |
| 124 | 0.4 |
| 131 | 1 |

Investigation of the substances for inhibition of HIV "Reverse Transcriptase"

The activity of reverse transcriptase (RT) was determined with the aid of a "Scintillation Proximity Assay" (SPA). The reagent kit for the RT-SPA was obtained from Amersham/Buchler (Braunschweig). The enzyme RT (from HIV cloned in E. coli) originated from HT-Biotechnology Ltd., Cambridge, UK.

Procedure:

The test was carried out in accordance with the method manual of the manufacturer Amersham—with the following modifications:

bovine serum albumin was added to the "assay" buffer to the final concentration of 0.5 mg/ml.

the test was carried out in Eppendorf reaction vessels with a batch volume of 100 ml.

the RT concentrate of the manufacturer (5000 U/ml) was diluted to an activity of 15 U/ml in tris-HCl buffer 20 mM; pH 7.2; 30% of glycerol.

the incubation time for the batches was 60 minutes (37° C.).

after the reaction had been stopped and after "development" with the bead suspension, 130 ml of the batch were transferred to 4.5 ml of tris-HCl buffer, 10 mM; pH 7.4; 0.15M NaCl, and the tritium activity was measured in a β-counter.

Testing of the substances:

For a preliminary test of the inhibitor activity, the substances were dissolved in dimethyl sulfoxide (stock solution c=1 mg/ml) and tested in a dilution in dimethyl sulfoxide of $10^{-1}$, $10^{-2}$, $10^{-3}$ and the like to determine $IC_{50}$ values, the inhibitor stock solutions were further diluted in tris-HCl buffer, 50 mM, pH 8 and tested in suitable concentrations. The concentration associated with 50% enzyme inhibition was determined from the graph of RT activity against Log $C_{inh}$.

Table 2 shows the results of the investigation.

TABLE 2

| Compound of Example No. | Reverse transcriptase assay $IC_{50}$ (µg/ml) |
|---|---|
| 2 | 0.022 |
| 3 | 0.004 |
| 4 | 0.01–0.1 |
| 5 | 0.001–0.01 |
| 6 | 0.001–0.01 |
| 7 | 0.006 |
| 8 | 0.01–0.1 |
| 9 | 0.001–0.01 |
| 10A | >10 |
| 10B | >10 |
| 12 | 0.01–0.1 |
| 16 | 0.1–1 |
| 20 | 1–10 |
| 21 | 0.1–1 |
| 23 | 0.1–1 |
| 24 | 0.01–0.1 |
| 27 | 1–10 |
| 29 | 1–10 |
| 30 | 0.1–1 |
| 32 | 0.1–1 |
| 33 | about 0.01 |
| 34 | 0.01–0.1 |
| 35 | 0.001–0.01 |
| 38 | 1–10 |
| 39 | 0.01–0.1 |
| 40 | 0.01–0.1 |
| 42 | 1–10 |
| 43 | 0.001–0.01 |
| 44 | about 0.01 |
| 45 | 0.001–0.01 |
| 47 | 0.01–0.1 |
| 48 | 0.001–0.01 |
| 49 | 0.1–1 |
| 50 | 0.01–0.1 |
| 51 | 0.01–0.1 |
| 52 | 0.01–0.1 |
| 62 | 0.001–0.01 |
| 67 | 0.01–0.1 |
| 70 | 0.001–0.01 |
| 78 | 0.01–0.1 |
| 82 | 0.01–0.1 |
| 87 | 0.01–0.1 |
| 103 | 0.01–0.1 |
| 104 | about 0.01 |
| 114 | 0.006 |
| 115 | 0.001–0.01 |
| 117 | 0.001–0.01 |

TABLE 2-continued

| Compound of Example No. | Reverse transcriptase assay IC$_{50}$ (μg/ml) |
| --- | --- |
| 119 | 0.001–0.01 |
| 120 | 0.001–0.01 |
| 123 | 0.001–0.01 |
| 124 | about 0.1 |
| 131 | 0.01–0.1 |
| 132 | about 0.1 |

The present invention is illustrated in more detail by the following examples and by the contents of the patent claims. Preparation of the starting materials

EXAMPLE I

6-Chloro-3,3-dimethyl-1,3-dihydroquinoline-2,4-dione

Lithium diisopropylamide was prepared at −70° C. from 7.3 g (0.072 mol) of diisopropylamine in 100 ml of anhydrous tetrahydrofuran and 45 ml of a 1.6M solution of n-butyllithium in hexane (0.072 mol). After warming briefly to −20° C., 3.48 g (0.03 mol) of ethyl isobutyrate was added, again at −70° C. The mixture was allowed to warm to 0° C. and was stirred at 0° C. for 30 minutes. The lithium compound was added dropwise to a suspension, cooled to −30° C., of 5.9 g (0.03 mol) of 5-chloroisatic anhydride in 50 ml of anhydrous tetrahydrofuran. The mixture was allowed to warm to 0° C. in the course of one hour, and the yellow reaction solution was poured onto 400 ml of ice-water. The mixture was extracted three times with ethyl acetate, and the combined organic phases were washed with one portion each of saturated aqueous sodium bicarbonate solution and saturated aqueous sodium chloride solution, dried over sodium sulfate and concentrated. After the residue had been stirred with ether/pentane, 5.1 g (76%) of the desired compound were obtained, melting point 211°–212° C. after crystallization from isopropanol.

$^1$H-NMR (200 MHz, d$_6$-DMSO): δ=1.30 (s, 6H), 7.11 (d, J=7.5 Hz, 1H), 7.6–7.7 (m, 2H), 10.87 ppm (s, 1H).
MS: (M+H)$^+$=224.

EXAMPLE II (3RS)-6-Chloro-3-ethyl-1,3-dihydroquinoline-2,4-dione

A suspension of 12.0 g (0.05 mol) of 3-ethylmalonic acid 4-chloroanilide in 110 g of polyphosphoric acid (about 84% of P$_2$O$_5$) was heated to 120° C., while stirring vigorously, and kept at this temperature for 45 minutes. During this procedure, the substance dissolved, the solution becoming yellow in coloration and foaming. When the reaction had ended, the reaction solution was poured onto about 200 ml of ice-water, while stirring, whereupon the product precipitated as a white solid. It was filtered off with suction, washed neutral with water and dried at 50° C. in vacuo. Yield: 8.3 g (75%) of melting point 228° C. (after recrystallization from isopropanol/heptane)

$^1$H-NMR (200 MHz, d$_6$-DMSO): δ=1.0 (t, J=7.5 Hz, 3H), 2.56 (q, J=7.5 Hz, 2H), 7.25 (d, J=9 Hz, 1H), 7.48 (dd, J=9, 2.5 Hz, 1H), 7.85 (d, J=2.5 Hz, 1H), 10.23 (s, 1H), 11.41 ppm (s, 1H).
MS: (M+H)$^+$=224

EXAMPLE III 3,3-Dimethyl-6-methoxy-1,3-dihydroquinoline-2,4-dione

Analogously to Example II, 16.2 g (80%) of the desired compound were obtained using 21.8 g (0.092 mol) of 3,3-dimethylmalonic acid 4-methoxyanilide. Melting point 169°–170 ° C. (after recrystallization from isopropanol)

$^1$H-NMR (200 MHz, d$_6$-DMSO): δ=1.31 (s, 6H), 3.78 (s, 3H), 7.02–7.28 (m, 3H), 10.62 ppm (s, 1H).
MS: (M+H)$^+$=220

Preparation of the end products

EXAMPLE 1 anti-6–Chloro-3,3-dimethyl-4-(hydroxyimino)-1,3-dihydroquinolin-2-one (A) and syn-6-chloro-3,3-dimethyl-4-(hydroxyimino)-1,3-dihydroquinolin-2-one (B)

A solution of 11.20 g (0.05 mol) of 6-chloro-3,3-dimethyl-1,3-dihydroquinoline-2,4-dione and 3.80 g (0.055 mol) of hydroxylamine hydrochloride was dissolved in 150 ml of anhydrous pyridine, and the solution was heated at 100° C. for 24 hours. The reaction mixture was then poured onto about 600 ml of ice-water, and the product which had precipitated was filtered off with suction, washed neutral with water and dried at 50° C. in vacuo. Crude-yield: 12.1 g of melting point 242° C. (decomposition).

7.6 g (64%) of the pure anti-isomer A were isolated by recrystallization from isopropanol/heptane and ethyl acetate/heptane. 290 mg (2.4%) of the pure syn-isomer B, in addition to 2.6 g (22%) of the syn/anti mixture, were to be obtained from the mother liquor by chromatographing twice on silica gel (ethyl acetate/heptane=2:1).

anti-6–Chloro-3,3-dimethyl-4-(hydroxyimino)-1,3-dihydroquinolin -2-one (A)

$^1$H-NMR (200 MHz, d$_6$-DMSO): δ=1.26 (s, 6H), 7.02 (d, J=9 Hz, 1H), 7.43 (dd, J=9, 2.5 Hz, 1H), 8.25 (d, J=2.5 Hz, 1H), 10.53 (s, 1H), 11.79 ppm (s, 1H)
MS: (M +H)$^+$: =239
UV (MeOH): λ$_{max}$ (ε)=224 (20 620), 250 (12 400), 320 nm (3 030)

syn-6-Chloro-3,3-dimethyl-4-(hydroxyimino)-1,3-dihydroquinolin-2-one (B)

$^1$H-NMR (200 MHz, d$_6$-DMSO): δ=1.60 (s, 6H), 6.94 (d, J=9 Hz, 1H), 7.33 (dd, J=9, 2.5 Hz, 1H), 7.75 (d, J=2.5 Hz, 1H), 10.48 (s, 1H), 11.68 ppm (s, 1H)
MS: (M+H)$^+$=239
UV (MeOH): λ$_{max}$ (ε)=221 (15 280), 227 (17 370), 247 (22 200), 329 nm (3 920)

EXAMPLE 2 anti-6-Chloro-3,3-dimethyl-4-(ethyloxyimino)-1,3-dihydroquinolin-2-one

A solution of 560 mg (2.5 mmol) of 6-chloro-3,3-dimethyl1,3-dihydroquinolin-2,4-dione (Example 1) and 370 mg (3.8 mmol) of 0-ethylhydroxylamine hydrochloride in 5 ml of pyridine was heated under reflux for 20 hours. It was then concentrated, the residue was taken up in ethyl acetate/water, the phases were separated and the organic phase was washed once with saturated aqueous sodium chloride solution. After drying (magnesium sulphate), the organic phase was concentrated and the residue was chromatographed on silica gel. 550 mg (82%) of the desired product were isolated as a white solid of melting point 186°–187° C. using ethyl acetate/heptane=1:2. According to the product contained 10% of the syn isomer. Recrystallization from ethyl acetate/heptane gave the pure anti isomer, melting point 190°–192° C.

$^1$H-NMR (270 MHz, DMSO-d$_6$): δ=1.33 (t, J=7 Hz, 3H), 1.41 (s, 6H), 4.23 (q, J=7 Hz, 2H), 6.76 (d, J=9 Hz, 1H), 7.29 (dd, J=9, 2.5 Hz, 1H), 7.88 (br, s, 1H), 8.28 ppm (d, J=2.5 Hz, 1H).
MS: (M+H)$^+$=267

EXAMPLE 3 anti-6-Chloro-3,3-dimethyl-4-(ethyloxyimino)-1,3-dihydroquinoline-2-thione 200 mg (0.5 mmol) of Lawesson reagent were added to a solution of 200 mg (0.8 mmol) of the compound of Example 2 in 10 ml of anhydrous toluene, and the mixture was heated at 100° C. for 1 hour. When the reaction had ended, the solvent was stripped off in vacuo and the residue was chromatographed on silica gel. 200 mg (88%) of the desired product were isolated as a yellow solid using acetone/heptane 1:3 as the eluting agent. Melting point 175° C. (after recrystallization from methyl t-butyl ether/heptane)

$^1$H-NMR (270 MHz, DMSO-$_6$): δ=1.25 (t, J=7 Hz, 3H), 1.41 (s, 6H), 4.19 (q, J=7 Hz, 2H), 7.28 (d, J=9 Hz, 1H), 7.56 (dd, J=9, 2.5 Hz, 1H), 8.13 (d, J=2.5 Hz, 1H), 12.55 ppm (br. s, 1H).

MS: (M+H)$^+$=283

EXAMPLE 4 syn-6-Chloro-3,3-dimethyl-4-(ethyloxyimino)-1,3-dihydroquinolin-2-one 1.32 g (5.03 mmol) of triphenylphosphine were added to a solution of 400 mg (1.68 mmol) of the compound of Example 1B in 10 ml of anhydrous tetrahydrofuran and 2 ml of absolute ethanol, while cooling to 0° C. A solution of 1.1 ml (6.95mmol) of diethyl azodicarboxylate in 2 ml of absolute ethanol was then slowly added dropwise, likewise at 0° C, and the mixture was stirred at 0° C. for a further 30 minutes and then at room temperature for 20 hours and concentrated. Chromatography on silica gel using ethyl acetate/heptane=1:3 as the eluting agent gave 310 mg (69%) of the desired compound as a white crystalline solid of melting point 206°–207° C.

$^1$H-NMR (200 MHz, DMSO-d$_6$): δ=1.28 (t, J=7 Hz, 3H), 1.58 (s, 6H), 4.22 (q, J=7 Hz, 1H), 6.96 (d, J=9 Hz, 1H), 7.37 (dd, J=9, 2.5 Hz, 1H), 7.80 (d, J=2.5 Hz, 1H), 10.55 ppm (br. s, 1H).

MS: (M+H)$^+$=267

EXAMPLE 5 syn-6-Chloro-3,3-dimethyl-4-(ethyloxyimino)-1,3-dihydroquinoline-2-thione

As described under Example 3, 200 mg(0.8 mmol) of the compound of Example 4 were sulfurized with Lawesson reagent. Chromatography on silica gel using ethyl acetate/heptane=1:5 as the eluting agent gave 180 mg (85%) of the desired compound, but as a 1:2 mixture with the anti-isomer of Example 3. (Isomerization occurs under heat.) Melting point 163°–164° C.

$^1$H-NMR (200 MHz, DMSO-d$_6$): δ=1.30 (t, J=7.5 Hz, 3H), 1.38 (s, 6H), 4.26 (q, J=7.5 Hz, 1H), 7.25 (d, J=9 Hz, 1 H), 7.45 (dd, J =9, 2.5 Hz, 1 H), 7.85 (d, J=2.5 Hz, 1H), 12.55 ppm (br. s, 1H).

MS: (M+H)$^+$=283

EXAMPLE 6 anti-6-Chloro-3,3-dimethyl-4-(isopropyloxyimino)-1,3dihydroquinolin-2-one 212 mg (4.4 mmol) of a 50% strength sodium hydride suspension in mineral oil were added to the compound of Example 1A (954 mg, 4.0 mmol) in 30 ml of anhydrous tetrahydrofuran, and the mixture was heated under reflux for 30 minutes. It was then cooled to room temperature, 0.86 ml (8.8 mmol) of 2-iodopropane was added, and the mixture was stirred under reflux for a further 26 hours. The reaction solution was then concentrated and the residue was chromatographed on silica gel (ethyl acetate/heptane=1:2). 560 mg (50%) of the desired product of melting point 207°–208° C. were isolated.

$^1$H-NMR (200 MHz, DMSO-d$_6$): δ=1.25 (d, J=7 Hz, 6H), 1.28 (s, 6H), 4.38 (sept., J=7H, 1H), 7.04 (d, J=9 Hz, 1H), 7.44 (dd, J=9, 2.5 Hz, 1H), 8.15 (d, J=2.5 Hz, 1H), 10.58 ppm (s, 1H)

MS: (M+H)$^+$=281

EXAMPLE 7 anti-6-Chloro-3,3-dimethyl-4-(isopropyloxyimino)-1,3-dihydroquinoline-2-thione

A suspension of 450 mg (1.6 mmol) of the compound of Example 6 in 30 ml of anhydrous toluene was heated under reflux with 357 mg (0.88 mmol) of Lawesson reagent for 2 hours. After removal of the solvent, the residue was purified on silica gel using ethyl acetate/heptane=1:3. The yield was 450 mg (94%) of crystalline solid of melting point 194° C.

$^1$H-NMR (200 MHz, DMSO-d$_6$): δ=1.24 (d, J=6 Hz, 6H), 1.38 (s, 6H), 4.40 (m, 1H), 7.28 (d, J=9 Hz, 1H), 7.55 (dd, J=9, 2.5 Hz, 1H), 8.16 (d, J=2.5 Hz, 1H), 12.54 ppm (s, 1H)

MS: (M+H)$^+$=297

EXAMPLE 8 anti-6-Chloro-3,3-dimethyl-4-(n-propyloxyimino)-1,3-dihydroquinolin-2-one

Analogously to Example 6, 500 mg (44%) of the desired compound of melting point 157° C. were isolated from the compound of Example 1A (954 mg, 4.0 mmol) and n-propyl iodide (2.0 ml, 20.0 mmol).

$^1$H-NMR (200 MHz, DMSO-d$_6$): δ=0.91 (t, J=7.5 Hz, 3H), 1.25 (s, 6 H), 1.66 (m, 2 H), 4.09 (t, J =7 Hz, 2 H), 7.04 (d, J=9 Hz, 1H), 7.46 (dd, J=9, 2.5 Hz, 1H), 8.13 (d, J=2.5 Hz, 1H), 10.58 ppm (s, 1H)

MS: (M+H)$^+$=281

EXAMPLE 9 anti-6-Chloro-3,3-dimethyl-4-(n-propyloxyimino)-1,3dihydroquinoline-2-thione

The compound of Example 8 (393 mg, 1.4 mmol) was sulfurized as described in Example 7. 370 mg (89% ) of the desired product of melting point 156° C. were obtained.

$^1$H-NMR (200 MHz, DMSO-d$_6$): δ=0.91 (t, J=7.5 Hz, 3H), 1.38 (s, 6H), 1.66 (m, 2H), 4.11 (t, J=6 Hz, 2H), 7.28 (d, J=9 Hz, 1H), 7.55 (dd, J=9, 2.5 Hz, 1H), 8.14 (d, J=2.5 Hz, 1H), 12.55 ppm (s, 1H)

MS: (M+H)$^+$=297

EXAMPLE 10 anti-4-(Benzyloxyimino)-6-chloro-3,3-dimethyl-1,3-dihydroquinoline-2-one (A) and anti-(1-benzyl)-4-(benzyloxyimino)6-chloro-3,3-dimethyl-1,3-dihydroquinolin-2-one (B)

212 mg (4.4 mmol) of a 50% strength suspension of sodium hydride in mineral oil were added to the compound of Example 1A (954 mg, 4.0 mmol) in 30 ml of anhydrous tetrahydrofuran, and the mixture was heated under reflux for 30 minutes. It was then cooled, 1.37 g (8.0 mmol) of benzyl bromide were added and the mixture was heated under reflux for a further 20 hours. The reaction solution was concentrated and the products were separated by chromatography on silica gel (ethyl acetate/heptane=1:3). After the eluates had been stirred with pentane, 580 mg (35%) of white crystalline compound 10B of melting point 143° C.

and 410 mg (31%) of white crystalline compound 10A of melting point 183° C. were obtained.

anti-4-(Benzyloxyimino)-6-chloro-3,3-dimethyl-1,3-dihydroquinolin-2-one (A)

$^1$H-NMR (200 MHz, DMSO-d$_6$): δ=1.26 (s, 6H), 5.20 (s, 2H), 7.03 (d, J=9.5 Hz, 1H), 7.2–7.5 (m, 6H), 8.13 (d, J=2.5 Hz, 1H), 10.60 ppm (s, 1H)

MS: (M+H)$^+$=329 anti-(1-Benzyl)-4-(benzyloxyimino)-6-chloro-3,3-dimethyl-1,3-dihydroquinolin-2-one (B)

$^1$H-NMR (200 MHz, DMSO-d$_6$): δ=1.35 (s, 6H), 5.14 (s, 2H), 5.21 (s, 2H), 7.1–7.5 (m, 12H), 8.10 ppm (d, J=2.5 Hz, 1H)

MS: (M+H)$^+$=419

EXAMPLE 11 anti-6-Chloro-3,3-dimethyl-4-hydrazono-1,3-dihydroquinolin-2-one

The compound of Example 1A (6.7 g, 0.03 mol) was suspended in 200 ml of anhydrous ethanol and, after addition of 14.5 ml (0.3 mol) of hydrazine hydrate (100% pure) and 2 g of pyridinium hydrochloride, the mixture was heated under reflux for 14 hours. The yellow reaction solution was concentrated and the solid residue was recrystallized from isopropanol. The yield was 3.3 g (46%) of melting point 228°–230° C.

$^1$H-NMR (200 MHz, DMSO-d$_6$): δ=1.17 (s, 6H), 6.66 (s, 2H), 7.02 (d, J=9 Hz, 1H), 7.36 (dd, J=9, 2.5 Hz, 1H), 7.86 (d, J=2.5 Hz, 1H), 10.38 ppm (s, 1H).

MS: (M+H)$^+$=238

EXAMPLE 12 anti-6-Chloro-3,3-dimethyl-4-(isopropylazino)-1,3-dihydroquinolin-2-one

The compound of Example 11 (950 rag, 4 mmol) was stirred with 30 ml each of acetone and methanol at room temperature for 2 hours. The mixture was then concentrated and the residue was recrystallized from heptane/ethyl acetate. Yield: 440 mg (40%) of melting point 184°–185° C.

$^1$H-NMR (200 MHz, DMSO-d$_6$): δ=1.31 (s, 6H), 1.86 (s, 3H), 2.02 (s, 3H), 7.02 (d, J=9 Hz, 1H), 7.43 (dd, J=9, 2.5 Hz, 1H), 7.83 (d, J=2.5 Hz, 1H), 10.58 ppm (s, 1H).

MS: (M+H)$^+$=306

EXAMPLE 13 anti-3,3-Dimethyl-4-(isopropenyloxycarbonyloxyimino)-6-methoxy-1,3-dihydroquinolin-2-one The compound of-Example 36 (936 rag, 4 mmol) was suspended in 50 ml of anhydrous methylene chloride, and 0.65 ml (8 mmol) of pyridine was added. 0.66 ml (6 mmol) of isopropenyl chloroformate was added dropwise, while cooling with ice, and the mixture was then stirred at room temperature. After 18 hours, it was washed with water and dried (sodium sulfate), and the crude product was recrystallized from diisopropyl ether. Yield 750 mg (59%) of melting point 145°–146° C.

$^1$H-NMR (200 MHz, DMSO-d$_6$): δ=1.34 (s, 6H), 1.95 (s, 3H), 3.77 (s, 3H), 4.88 (s, 2H), 7.03 (d, J=9 Hz, 1H), 7.16 (dd, J=9, 3 Hz, 1H), 7.53 (d, J=3 Hz, 1H), 10.51 ppm (s, 1H).

MS: (M+H)$^+$=319

EXAMPLE 13a anti-6-Chloro-3,3,-dimethyl-4-(ethyloxyimino)-2-hydroxyimino-1,3-dihydroquinoline (see also Example 70 in Table 3)

417 mg (6 mmol, 2 equivalents) of hydroxylamine hydrochloride and 0.83 ml (6 mmol, 2 equivalents) of triethylamine were added at 25° C. to a suspension of 848 mg (3 mmol) of the compound of Example 3 (anti-6-chloro-3,3-dimethyl-4-(ethyloxyimino)-1,3-dihydroquinoline-2-thione) in 30 ml of anhydrous ethanol. The reaction mixture was stirred at 25° C. for 18 hours. When the reaction had ended, the solvent was stripped off in vacuo and the residue was taken up in 150 ml of ethyl acetate. The organic phase was extracted twice with 75 ml of water in each case and dried by means of sodium sulfate, and the solvent was removed in vacuo. The crude product obtained in this way was triturated with n-pentane. 810 mg (2.88 mmol) of the desired compound (yield 96%) of melting point 192°–193° C. (R$_f$: 0.25; eluent; n-heptane/ethyl acetate 3:1) were obtained.

$^1$H-NMR (270 MHz, d$_6$-DMSO: δ=1,23 (t, J=7.6 Hz, 3H), 1,25 (s, 6H), 4.15 (d, J=7.6 Hz, 2H), 7.28 (d, J=8 Hz, 1H), 7.34 (dd, J=8, 2.5 Hz, 1H), 8.02 (d, J=2.5 Hz, 1H), 9.33 (br. s, 1H), 10.13 (br. s, 1H)

MS: (M+H)$^+$=282

EXAMPLE 13b anti-6-Chloro-3,3-dimethyl-2-(methylamino)-quinoline-4(3H)-one-4-O-ethyl oxime (see also Example 127 in Table 3)

5 ml of 40% aqueous methylamine solution (71.4 mmol) were added at 25° C. to a suspension of 1.41 g (5 mmol) of the compound of Example 3 (anti-6-chloro-3,3-dimethyl-4-(ethyloxyimino)-1,3-dihydroquinoline-2-thione) in 50 ml of anhydrous ethanol. The reaction mixture was stirred under reflux conditions for 8 hours. When the reaction had ended, the solvent was stripped off in vacuo and the residue was chromatographed on silica gel. Using ethyl acetate/n-heptane 1:1 as the eluent, 550 mg (1.97 mmol; 39%) of the desired product were isolated as a colorless solid of melting point 112° C. (R$_f$: 0.51; eluent: ethyl acetate/n-heptane 1:1).

$^1$H-NMR (200 MHz, d$_6$-DMSO: δ=1,26 (t, J=7.5 Hz, 3H), 1.25 (s, 6H), 2.79 (d, J=4.5 Hz, 3H), 4.14 (q, J=7.5 Hz, 2H), 6.98 (d, J=9 Hz, 1H), 7.16 (br. q, J=4.5 Hz, 1H), 7.28 (dd, J=3.9 Hz, 1H), 8.05 (d, J=3Hz, 1H)

MS: (M+H)$^+$=280

The examples listed in Table 3 were prepared analogously to the procedures of Examples 1–13b:

TABLE 3

| Ex. No. | R$^1$ | R$^2$ | R$^3$ | R$^4$ | X | Y | M.p. [°C.] |
|---|---|---|---|---|---|---|---|
| 14 | 6-Cl | Me | Me | Me | O | —OMe | 117 |
| 15 | 6-Cl | Et | Me | Me | O | —OEt | oil |
| 16 | 6-Cl | H | Me | Me | S | —OBn | 154 |
| 17 | 6-Cl | H | Me | Me | O | —O(2-Me—Bn) | 164 |
| 18 | 6-Cl | H | Me | Me | S | —O(2-Me—Bn) | 188 |
| 19 | 6-Cl | 2-Me—Bn | Me | Me | O | —O(2-Me—Bn) | 144 |

TABLE 3-continued

| Ex. No. | R¹ | R² | R³ | R⁴ | X | Y | M.p. [°C.] |
|---|---|---|---|---|---|---|---|
| 20 | 6-Cl | H | Me | Me | O | —O(2-NO₂—Bn) | 144–147 |
| 21 | 6-Cl | H | Me | Me | S | —O(2-NO₂—Bn) | 182 |
| 22 | 6-Cl | 2-NO₂—Bn | Me | Me | O | —O(2-NO₂—Bn) | 136–137 |
| 23 | 6-Cl | H | Me | Me | O | —O(3-Cl—Bn) | 178 |
| 24 | 6-Cl | H | Me | Me | S | —O(3-Cl—Bn) | 139 |
| 25 | 6-Cl | 3-Cl—Bn | Me | Me | O | —O(3-Cl—Bn) | 113 |
| 26 | 6-Cl | H | Me | Me | O | —O(4-Cl—Bn) | 197 |
| 27 | 6-Cl | H | Me | Me | S | —O(4-Cl—Bn) | 152 |
| 28 | 6-Cl | 4-Cl—Bn | Me | Me | O | —O(4-Cl—Bn) | 129–130 |
| 29 | 6-Cl | H | Me | Me | O | —O(2-Cl—Bn) | 186 |
| 30 | 6-Cl | H | Me | Me | S | —O(2-Cl—Bn) | 183 |
| 31 | 6-Cl | 2-Cl—Bn | Me | Me | O | —O(2-Cl—Bn) | 169–171 |
| 32 | 6-Cl | H | Me | Me | O | —OC₂H₄OMe | 158 |
| 33 | 6-Cl | H | Me | Me | S | —OC₂H₄OMe | 166 |
| 34 | 6-Cl | H | Me | Me | O | —OMe | 167 |
| 35 | 6-Cl | H | Me | Me | S | —OMe | 179 |
| 36 | 6-MeO | H | Me | Me | O | —OH | 239 |
| 37 | 6-MeO | H | Me | Me | O | —OEt | 154 |
| 38 | 6-Cl | H | Et | H | O | —OH | 236–238 |
| 39 | 6-Cl | H | Et | H | O | —OEt | 188–189 |
| 40 | 6-Cl | H | Et | H | O | —OiPr | 186–188 |
| 41 | 6-Cl | H | Et | H | O | H | 259–260 |
| 42 | 6-Cl | H | Et | H | S | H | >240 |
| 43 | 6-MeO | H | Me | Me | S | —OEt | 146 |
| 44 | 6-MeO | H | Me | Me | O | —OiPr | 182 |
| 45 | 6-MeO | H | Me | Me | S | —OiPr | 177 |
| 46 | 6-MeO | H | Me | Me | S | —O—CO—OC(Me)=CH₂ | 168–169 |
| 47 | 6-Cl | H | Me | Me | O | —O—CH₂CH=CH₂ | 151 |
| 48 | 6-Cl | H | Me | Me | S | —O—CH₂CH=CH₂ | 149 |
| 49 | 6-Cl | H | Me | Me | O | —O—C₂H₄SMe | 149 |
| 50 | 6-Cl | H | Me | Me | S | —O—C₂H₄SMe | 127 |
| 51 | 6-Cl | H | Me | Me | O | —O—CH₂C≡CH | 176 |
| 52 | 6-Cl | H | Me | Me | O | —O—CH(Me)C₂H₅ | 145 |
| 53 | 6-MeO | H | Me | Me | O | —O—COCH₃ | 178–179 |
| 54 | 6-Meo | H | Me | Me | S | —O—COCH₃ | 150–152 |
| 55 | 6-MeO | H | Me | Me | O | —O—CO—OC(CH₃)₂ | 154 |
| 56 | 6-MeO | H | Me | Me | S | —O—CO—OC(CH₃)₂ | 150 |
| 57 | 6-MeO | H | CH₃ | CH₃ | O | O—COiPr | 154 |
| 58 | 6-MeO | H | CH₃ | CH₃ | S | O—COiPr | 160 |
| 59 | 6-MeO | H | CH₃ | CH₃ | O | OCO—C(CH₃)=CH₂ | 146 |
| 60 | 6-MeO | H | CH₃ | CH₃ | S | OCO—C(CH₃)=CH₂ | 169 |
| 61 | 6-Cl | H | CH₃ | CH₃ | NOiPr | OiPr | 64 |
| 62 | 6-Cl | H | CH₃ | CH₃ | S | —N=C(CH₃)₂ | 201 |
| 63 | 6-OMe | H | CH₃ | CH₃ | O | OCOCH₃ | 179 |
| 64 | 6-Cl | H | CH₃ | CH₃ | O | O-(2-pyridyl) | 183 |
| 65 | 6-OMe | H | CH₃ | CH₃ | O | O—CH₂Ph | 145 |
| 66 | 6-Cl | H | CH₃ | CH₃ | S | O-(2-pyridyl) | 187 |
| 67 | 6-Cl | H | CH₃ | CH₃ | S | O—CH(CH₃)C₂H₅ | 160 |
| 68 | 6-MeO | H | CH₃ | CH₃ | O | O-(2-CH₂C₅H₄N) | 139 |
| 69 | 6-MeO | H | CH₃ | CH₃ | S | O-(2-CH₂C₅H₄N) | 143–144 |
| 70 | 6-Cl | H | CH₃ | CH₃ | NOH | O—C₂H₅ | 192–193 |
| 71 | 6-OC₂H₅ | H | CH₃ | CH₃ | O | O—C₂H₅ | 133–135 |
| 72 | 6-Cl | H | CH₃ | CH₃ | NOC₂H₅ | O—C₂H₅ | resin |
| 73 | 6-Cl | H | CH₃ | CH₃ | N—OiPr | O—C₂H₅ | 80–81 |
| 74 | 6-n-C₄H₉O | H | CH₃ | CH₃ | O | OC₂H₅ | 111 |
| 75 | 6-n-C₄H₉O | H | CH₃ | CH₃ | O | OiPr | 133 |
| 76 | 6-C₂H₅O | H | CH₃ | CH₃ | S | OC₂H₅ | 141–144 |
| 77 | 6-MeS | H | CH₃ | CH₃ | O | OC₂H₅ | 116–117 |
| 78 | 6-MeS | H | CH₃ | CH₃ | O | OiPr | 134–135 |
| 79 | 6-n-C₄H₉O | H | CH₃ | CH₃ | S | OC₂H₅ | 134 |
| 80 | 6-n-C₄H₉O | H | CH₃ | CH₃ | S | OiPr | 159 |
| 81 | 6-MeS | H | CH₃ | CH₃ | S | OC₂H₅ | 133 |
| 82 | 6-MeS | H | CH₃ | CH₃ | S | OiPr | 154 |
| 83 | 6-CF₃O | H | CH₃ | CH₃ | O | OC₂H₅ | 68–69 |
| 84 | 6-CF₃O | H | CH₃ | CH, | S | OC₂H₅ | 127 |
| 85 | 6-CF₃O | H | CH₃ | CH₃ | O | OiPr | 168–169 |
| 86 | 6-MeO | H | CH₃ | CH₃ | NOH | OC₂H₅ | 144–150 |
| 87 | 6-CF₃O | H | CH₃ | CH₃ | S | OiPr | Harz |
| 88 | 6-MeO | H | CH₃ | CH₃ | O | N-phenyl | 193 |
| 89 | 6-MeO | H | CH₃ | CH₃ | S | N-phenyl | 230 |
| 90 | 6-iPr | H | CH₃ | CH₃ | O | OC₂H₅ | 103–105 |
| 91 | 6-iPr | H | CH₃ | CH₃ | S | OC₂H₅ | 94–95 |
| 92 | 6-iPr | H | CH₃ | CH₃ | NOH | OC₂H₅ | 163–165 |
| 93 | 6-morpholin-4-yl | H | CH₃ | CH₃ | O | OC₂H₅ | 181–183 |
| 94 | 6-morpholin-4-yl | H | CH₃ | CH₃ | S | OC₂H₅ | 172–173 |
| 95 | 6-cyclohexyl | H | CH₃ | CH₃ | O | OiPr | 175–176 |

TABLE 3-continued

| Ex. No. | R$^1$ | R$^2$ | R$^3$ | R$^4$ | X | Y | M.p. [°C.] |
|---|---|---|---|---|---|---|---|
| 96 | 6-cyclohexyl | H | CH$_3$ | CH$_3$ | S | OiPr | 160–161 |
| 97 | 6-cyclohexyl | H | CH$_3$ | CH$_3$ | O | OC$_2$H$_5$ | 130 |
| 98 | 6-cyclohexyl | H | CH$_3$ | CH$_3$ | S | OC$_2$H$_5$ | 153–154 |
| 99 | 6-phenyl | H | CH$_3$ | CH$_3$ | O | OC$_2$H$_5$ | 176 |
| 100 | 6-phenyl | H | CH$_3$ | CH$_3$ | S | OC$_2$H$_5$ | 169 |
| 101 | 6-Cl | H | CH$_3$ | CH$_3$ | O | N=CH-phenyl | 185 |
| 102 | 6-Cl | H | CH$_3$ | CH$_3$ | S | N=CH-phenyl | 179 |
| 103 | 6-pyrid-4-ylmethyl | H | CH$_3$ | CH$_3$ | O | OC$_2$H$_5$ | 137 |
| 104 | 6-pyrid-4-ylmethyl | H | CH$_3$ | CH$_3$ | S | OC$_2$H$_5$ | 205 |
| 105 | 6-MeO | H | CH$_3$ | CH$_3$ | O | N=C(CH$_3$)$_2$ | 113–115 |
| 106 | 6-Cl | H | CH$_3$ | CH$_3$ | O | N=C(Et)$_2$ | 142 |
| 107 | 6-Cl | H | CH$_3$ | CH$_3$ | O | N=Cyclopentyl | 210 |
| 108 | 6-Cl | H | CH$_3$ | CH$_3$ | S | NH$_2$ | 238 |
| 109 | 6-Cl | H | CH$_3$ | CH$_3$ | NOH | OH | 203–204 |
| 110 | 6-Cl | H | CH$_3$ | CH$_3$ | S | N=C(Et)$_2$ | 145 |
| 111 | 6-Cl | H | —(CH$_2$)$_5$— | | O | OC$_2$H$_5$ | 216 |
| 112 | 6-Cl | H | —(CH$_2$)$_5$— | | S | OC$_2$H$_5$ | 202 |
| 113 | 6-Cl | H | —(CH$_2$)$_5$— | | NOH | OC$_2$H$_6$ | 205 |
| 114 | 6-Cl | H | —(CH$_2$)$_3$— | | O | OC$_2$H$_5$ | 168–174 |
| 115 | 6-Cl | H | —(CH$_2$)$_3$— | | S | OC$_2$H$_5$ | 160–162 |
| 116 | 6-Cl | H | —(CH$_2$)$_3$— | | O | OiPr | 180 |
| 117 | 6-Cl | H | —(CH$_2$)$_4$— | | S | OiPr | 200 |
| 118 | 6-Cl | H | C$_2$H$_5$ | C$_2$H$_5$ | O | OC$_2$H$_5$ | 138 |
| 119 | 6-Cl | H | C$_2$H$_5$ | C$_2$H$_5$ | O | OiPr | 143 |
| 120 | 6-Cl | H | —(CH$_2$)$_3$— | | S | OiPr | 178 |
| 121 | 6-Cl | H | —(CH$_2$)$_4$— | | O | OC$_2$H$_5$ | 180 |
| 122 | 6-Cl | H | —(CH$_2$)$_4$— | | S | OC$_2$H$_5$ | 164 |
| 123 | 6-Cl | H | —(CH$_2$)$_4$— | | O | OiPr | 189 |
| 124 | 6-OE+ | H | CH$_3$ | CH$_3$ | NOH | NOC$_2$H$_5$ | 103–105 |
| 125* | 6-MeO | H | CH$_3$ | CH$_3$ | N—CH | OiPr | 100–102 |
| 126* | 6-Cl | H | CH$_3$ | CH$_3$ | N-n-butyl | OC$_2$H$_5$ | 40 |
| 127* | 6-Cl | H | CH$_3$ | CH$_3$ | N—CH$_3$ | OC$_2$H$_5$ | 112 |
| 128* | 6-MeO | H | CH$_3$ | CH$_3$ | N-benzyl | OiPr | 68–69 |
| 129* | 6-Cl | H | CH$_3$ | CH$_3$ | N—CH$_2$—CH$_2$OH | OC$_2$H$_5$ | 119 |
| 130* | 6-Cl | H | CH$_3$ | CH$_3$ | N-benzyl | OC$_2$H$_5$ | 101 |
| 131* | 6-Cl | H | CH$_3$ | CH$_3$ | N-phenyl | OC$_2$H$_5$ | oil |
| 132* | 6-Cl | H | CH$_3$ | CH$_3$ | N-(4-Cl-phenyl) | OC$_2$H$_5$ | oil |
| 133* | 6-cyclohexyl | H | CH$_3$ | CH$_3$ | N—CH$_3$ | OC$_2$H$_5$ | oil |
| 134* | 6-phenyl | H | CH$_3$ | CH$_3$ | N—CH$_3$ | OC$_2$H$_5$ | oil |
| 135 | 6-MeO | H | CH$_3$ | CH$_3$ | O | OC(O)N(CH$_3$)$_2$ | 228 |
| 136 | 6-MeO | H | CH$_3$ | CH$_3$ | O | OC(O)—(CH$_2$)$_2$—CO$_2$H | oil |

*in the examples marked with * the reaction product is present as a compound of the tautomeric form Ia according to the $^1$H-NMR spectrum

We claim:

1. A compound of the formula I

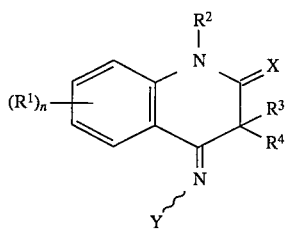
(I)

or a tautomeric form thereof, of the formula Ia, Ib or Ic

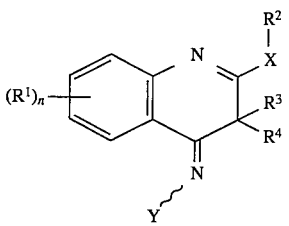
(Ia)

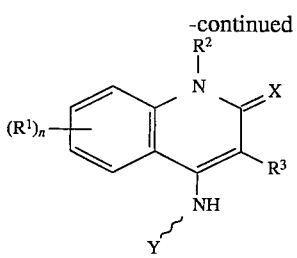
(Ib)

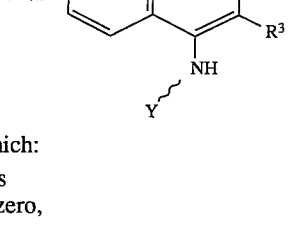
(Ic)

in which:

n is
zero,
one,
two, three
or four, the individual substituents R1 independently of one another are fluorine, chlorine, bromine, iodine, trifluoromethyl, trifluoromethoxy, hydroxyl, alkyl, cycloalkyl, alkoxy, alkoxy(alkoxy), alkylthio, alkylsulfinyl, alkylsulfonyl, nitro, amino, azido, alkylamino, dialkylamino, piperidino, morpholino, 1-pyrrolidinyl, acyl, acyloxy, acylamino, cyano, carbamoyl, carboxyl, alkyloxycarbonyl, hydroxysulfonyl or sulfamoyl or a phenyl, phenoxy, phenoxycarbonyl, phenylthio, phenylsulfinyl, phenylsulfonyl, phenoxysulfonyl, phenyl-sulfonyl, anilinosulfonyl, phenylsulfonylamino, benzoyl, morpholine, or pyridine radical which is optionally substituted by up to five radicals R5 which are independent of one another, in which R5 can be fluorine, chlorine, bromine, iodine, cyano, trifluoro-methyl, trifluoromethoxy, nitro, amino, azido, alkyl, cycloalkyl, alkoxy, alkylthio, alkylsulfinyl, alkyl-sulfonyl, alkylamino, dialkylamino, alkyloxycarbonyl, phenyl or phenoxy, X is oxygen, sulfur or substituted nitrogen N—R2 or N—O—R2, in which R2 can have the meanings given below, Y is R6, O—R6, S—R6, N—R6R7, N=C—R6R7 or C—R6R7R8, in which R6, R7 and R8 can have the meanings given below, R2, R6, R7 and R8 can be identical or different and can be, independently of one another, hydrogen, alkyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkyl-sulfonyl, phenylsulfonyl, oxo, thioxo, carboxyl or carbamoyl;

alkenyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkyl-sulfonyl, phenylsulfonyl, oxo, thioxo, carboxyl or carbamoyl;

alkynyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkyl-sulfonyl, phenylsulfonyl, oxo, thioxo, carboxyl or carbamoyl;

cycloalkyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkyl-sulfonyl, phenylsulfonyl, oxo, thioxo, carboxyl or carbamoyl;

cycloalkenyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkyl)-(alkyl), which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

(cycloalkenyl)-(alkyl), which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsulfonyl, phenylsulfonyl, oxo, thioxo, carboxyl or carbamoyl;

alkylcarbonyl, which is optionally substituted by fluorine, chlorine, bromine, iodine, cyano, amino, mercapto, hydroxyl, acyloxy, benzoyloxy, benzyloxy, phenoxy, alkoxy, alkylamino, dialkylamino, alkylthio, alkylsutfonyl, phenylsulfonyl, oxo, thioxo, carboxyl or carbamoyl;

alkenylcarbonyl, which is optionally substituted by fluorine, chlorine or hydroxyl, alkoxy, oxo or phenyl;

(cycloalkyl)carbonyl, which is optionally substituted by fluorine, chlorine or hydroxyl, alkoxy, oxo or phenyl;

(cycloalkenyl)carbonyl, which is optionally substituted by fluorine, chlorine or hydroxyl, alkoxy, oxo or phenyl;

(cycloalkyl)-(alkyl)carbonyl, which is optionally substituted by fluorine, chlorine or hydroxyl, alkoxy, oxo or phenyl;

(cycloalkenyl)-(alkyl)carbonyl, which is optionally substituted by fluorine, chlorine or hydroxyl, alkoxy, oxo or phenyl;

alkyloxycarbonyl, which is optionally substituted by fluorine, chlorine, bromine, hydroxyl, alkoxy, alkyl-amino, diatkylamino or alkylthio;

alkenyloxycarbonyl, which is optionally substituted by fluorine, chlorine, hydroxyl, alkoxy, oxo or phenyl;

alkynyloxycarbonyl, which is optionally substituted by fluorine, chlorine, hydroxyl, alkoxy, oxo or phenyl;

alkylthiocarbonyl, which is optionally substituted by fluorine, chlorine, hydroxyl, alkoxy, oxo or phenyl;

alkenylthiocarbonyl, which is optionally substituted by fluroine, chlorine, hydroxyl, alkoxy, oxo or phenyl;

alkylamino- or dialkylaminocarbonyl, which is optionally substituted by fluorine, chlorine, hydroxyl, alkoxy, oxo or phenyl;

alkenylamino- or dialkenylaminocarbonyl, which is option-ally substituted by fluorine, chlorine, hydroxyl, alkoxy, oxo or phenyl;

alkylsulfonyl, which is optionally substituted by fluorine, chlorine, hydroxyl, alkoxy, alkylthio, oxo or phenyl;

alkenylsulfonyl, which is optionally substituted by fluorine, chlorine, hydroxyl, alkoxy, oxo or phenyl;

or aryl, arylcarbonyl, aryl(thiocarbonyl), (arylthio)-carbonyl, (arylthio)thiocarbonyl, aryloxycarbonyl, (arylamino)thiocarbonyl, arylsulfonyl, arylalkyl, aryl-alkenyl, arylalkynyl, arylalkylcarbonyl, arylalkenyl carbonyl or arylalkoxycarbonyl, which are substituted by up to five radicals R5 which are independent of one another, in which R5 is as defined above;

or morpholine, or pyridine, with the proviso that R2 is not a hetero compound, and R3 and R4 are identical or different and independently of one another are hydrogen, alkyl, which is optionally substituted by fluorine, chlorine, hydroxyl, amino, mercapto, acyloxy, benzoyloxy, benzyloxy, phenoxy, alkoxy, alkylamino, dialkylamino, alkylthio, alkylsulfonyl, alkylsulfinyl, carboxyl or carbamoyl;

or $C_{3-5}$ cyclo-spiro;

in which, in the tautomeric forms of formulas Ib and Ic, R4 of the compound of formula I is hydrogen;

or an optical isomer thereof, a diastereomer in the pure form or in the form of a mixture of diastereomers, or an addition salt thereof, with the exception of the compounds in which, simultaneously, R3 and/or R4 are hydrogen and Y is R6 or CR6R7R8 and the compounds in which, simultaneously, R1 is Cl, R2 is H or CH3, R3 is OH, R4 is phenyl, X is O and Y is H or OH.

* * * * *

UNITED STATES PATENT AND TRADEMARK OFFICE
CERTIFICATE OF CORRECTION

PATENT NO. : 5,602,146
DATED : February 11, 1997
INVENTOR(S) : Uta-Maria BILLHARDT-TROUGHTON et al.

It is certified that error appears in the above-indentified patent and that said Letters Patent is hereby corrected as shown below:

Claim 1, column 34, line 2, "dialkylarnino," should read --dialkylamino,--.

Claim 1, column 34, lines 15-16, "alkylsutfonyl" should read --alkylsulfonyl--.

Claim 1, column 34, line 36, "diatkylamino" should read --dialkylamino--.

Claim 1, column 34, line 46, "fluroine" should read --fluorine--.

Signed and Sealed this

Twenty-ninth Day of July, 1997

Attest:

BRUCE LEHMAN

Attesting Officer

Commissioner of Patents and Trademarks